US00RE47471E

(19) United States
(12) Reissued Patent
de Haan et al.

(10) Patent Number: US RE47,471 E
(45) Date of Reissued Patent: Jul. 2, 2019

(54) HEAT-STABLE RESPIRATORY SYNCYTIAL VIRUS F PROTEIN OLIGOMERS AND THEIR USE IN IMMUNOLOGICAL COMPOSITIONS

(71) Applicant: Mucosis B.V., Groningen (NL)

(72) Inventors: Cornelis Alexander Maria de Haan, Utrecht (NL); Petrus Josephus Marie Rottier, Utrecht (NL); Bert Jan Haijema, Groningen (NL)

(73) Assignee: Mucosis B.V., Groningen (NL)

(21) Appl. No.: 15/081,854

(22) Filed: Mar. 26, 2016

Related U.S. Patent Documents

Reissue of:
(64) Patent No.: 9,060,975
Issued: Jun. 23, 2015
Appl. No.: 13/828,667
Filed: Mar. 14, 2013

(51) Int. Cl.
*A61K 39/155* (2006.01)
*C07K 14/005* (2006.01)
*C07K 19/00* (2006.01)
*A61K 39/12* (2006.01)

(52) U.S. Cl.
CPC ..... *A61K 39/155* (2013.01); *A61K 39/12* (2013.01); *C07K 14/005* (2013.01); *C12N 2760/18511* (2013.01); *C12N 2760/18534* (2013.01)

(58) Field of Classification Search
CPC ..... C07K 14/135; A61K 31/155
See application file for complete search history.

(56) References Cited

U.S. PATENT DOCUMENTS 7,312,311 B2 12/2007 Buist et al.
2012/0070446 A1 3/2012 Beaumont et al.

FOREIGN PATENT DOCUMENTS

WO 20021101026 A2 12/2002
WO 2008/147196 A2 12/2008
WO 2010/149743 A2 12/2010
WO 20101149745 A1 12/2010
WO WO 2011/008974 * 1/2011
WO 20121128628 A1 9/2012
WO 2012/158613 A1 11/2012
WO WO 2012/158613 * 11/2012

OTHER PUBLICATIONS

Matthew J. Betts and Robert B. Russell. Amino Acid Properties and Consequences of Substitutions, in Bioinformatics for Geneticists. Edited by Michael R. Barnes and Ian C. Gray 2003 John Wiley & Sons, Ltd., pp. 289-316.*

Thomas GM Schmidt & Arne Skerra.The Strep-tag system for one-step purification and high-affinity detection or capturing of proteins. 2007 Nature Protocols vol. 2 No. 6 pp. 1528-1535.*

Duckert, Brunak and Blom, "Prediction of proprotein convertase cleavage sites," Protein Engineering, Design & Selection vol. 17 No. 1,pp. 107±112, 2004.

Russell et al., "A Dual-Functional Paramyxovirus F Protein Regulatory Switch Segment: Activation and Membrane Fusion", The Journal of Cell Biology, vol. 163, No. 2, Oct. 27, 2003, pp. 363-374.

McLellan et al., "Structure-Based Design of a Fusion Glycoprotein Vaccine for Respiratory Syncytial Virus", Science, vol. 342, Nov. 1, 2013, pp. 592-598.

Collins et al., "Progress in Understanding and Controlling Respiratory Syncytial Virus: Still Crazy After All These Years", Virus Research, vol. 162, Issues 1-2, Dec. 2011, pp. 80-99.

McLellan et al., "Structure of Respiratory Syncytial Virus Fusion Glycoprotein in the Postfusion Conformation Reveals Preservation of Neutralizing Epitopes", Journal of Virology, vol. 85, No. 15, Aug. 2011, pp. 7788-7796.

Swanson et al., "Structural Basis for Immunization with Postfusion Respiratory Syncytial Virus Fusion F Glycoprotein (RSV F) to Elicit High Neutralizing Antibody Titers", PNAS, vol. 108, No. 23, Jun. 7, 2011, pp. 9619-9624.

Groothuis et al., "Prevention of Serious Respiratory Syncytial Virus-Related Illness. I: Disease Pathogenesis and Early Attempts at Prevention", Advances in Therapy, vol. 28, No. 2, Feb. 2011, pp. 91-109.

Hurwitz, "Respiratory Syncytial Virus Vaccine Development", Expert Review of Vaccines, vol. 10, No. 10, Oct. 2011, pp. 1415-1433.

Beeler et al., "Neutralization Epitopes of the F Glycoprotein of Respiratory Syncytial Virus: Effect of Mutation Upon Fusion Function", Journal of Virology, vol. 63, No. 7, Jul. 1989, pp. 2941-2950.

Groothuis et al., "Prevention of Serious Respiratory Syncytial Virus-Related Illness. II: Immunoprophylaxis", Advances in Therapy, vol. 28, No. 2, Feb. 2011, pp. 110-125.

Magro et al., "Neutralizing Antibodies against the Preactive Form of Respiratory Syncytial Virus Fusion Protein Offer Unique Possibilities for Clinical Intervention", Proceedings of the National Academy of Sciences of the United States of America, vol. 109. No. 8, Feb. 21, 2012, pp. 3089-3094.

Van Roosmalen et al., "Mucosal Vaccine Delivery of Antigens Tightly Bound to an Adjuvant Particle Made from Food-Grade Bacteria", Methods, vol. 38, Issue 2, Feb. 2006, pp. 144-149.

(Continued)

*Primary Examiner* — Bruce R Campell
(74) *Attorney, Agent, or Firm* — N.V. Nederlandsch Octrooibureau; Catherine A. Shultz; Tamara C. Stegmann

(57) ABSTRACT

Heat-stable oligomeric recombinant polypeptides, presenting at least one antigenic epitope of the pre-fusion Respiratory Syncytial Virus (RSV) F protein, comprising the RSV F protein ectodomain, functionally deleted in the HRB region, transmembrane and cytoplasmic domains replaced with a heterologous trimerization domain, and absent two functional multibasic furin cleavage sites, are useful as antigenic components in immunogenic compositions useful in methods of inducing an immune response and vaccinate against RSV infections.

25 Claims, 27 Drawing Sheets

Specification includes a Sequence Listing.

(56) References Cited

OTHER PUBLICATIONS

Harbury et al., "A Switch Between Two-, Three-, and Four-Stranded Coiled Coils in GCN4 Leucine Zipper Mutants", Science, New Series, vol. 262, No. 5138, Nov. 16, 1993, pp. 1401-1407.
González-Reyes et al., "Cleavage of the Human Respiratory Syncytial Virus Fusion Protein at Two Distinct Sites is Required for Activation of Membrane Fusion", Proceedings of the National Academy of Sciences of the United States of America, vol. 98, No. 17, Aug. 14, 2001, pp. 9859-9864.
Ruiz-Argüello et al., "Effect of Proteolytic Processing at Two Distinct Sites on Shape and Aggregation of an Anchorless Fusion Protein of Human Respiratory Syncytial Virus and Fate of the Intervening Segment", Journal of Virology, vol. 298, No. 2, Aug. 2002, pp. 317-326.
Ruiz-Argüello et al., "Thermostability of the Human Respiratory Syncytial Virus Fusion Protein Before and After Activation: Implications for the Membrane-Fusion Mechanism", Journal of Virology, vol. 85, No. 12, Dec. 2004, pp. 3677-3687.
Dormitzer et al., "Structural Vaccinology Starts to Deliver", Nature Reviews Microbiology 10, Dec. 2012, pp. 807-813.
Yin et al., "Structure of the Parainfluenza Virus 5 F Protein in its Metastable, Prefusion Conformation", Nature, vol. 439, Jan. 5, 2006 pp. 38-44.
De Vries et al., "The Influenza A Virus Hemagglutinin Glycosylation State Affects Receptor-Binding Specificity", Journal of Virology, vol. 403, No. 1, Jul. 20, 2010, pp. 17-25.
Wei et al., "Comparative Efficacy of Neutralizing Antibodies Elicited by Recombinant Hemagglutinin Proteins from Avian H5N1 Influenza Virus", Journal of Virology, vol. 82, No. 13, Jul. 2008, pp. 6200-6208.
Yang et al., "Characterization of Stable, Soluble Trimers Containing Complete Ectodomains of Human Immunodeficiency Virus Type 1 Envelope Glycoproteins", Journal of Virology, vol. 74, No. 12, 2000, pp. 5716-5725.
Cornelissen et al., "A Single Immunization with Soluble Recombinant Trimeric Hemagglutinin Protects Chickens against Highly Pathogenic Avian Influenza Virus H5N1", Public Library of Science, vol. 5, No. 5, May 2010, 9 pages.
De Vries et al., "Only Two Residues are Responsible for the Dramatic Difference in Receptor Binding Between Swine and New Pandemic H1 Hemagglutinin", Journal of Biological Chemistry, vol. 286, Feb. 18, 2011, pp. 5868-5875.
Tan et al., "Genetic Variability Among Complete Human Respiratory Syncytial Virus Subgroup A Genomes: Bridging Molecular Evolutionary Dynamics and Epidemiology", Public Library of Science, vol. 7, No. 12, Dec. 2012, 15 pages.
McLellan et al., "Structure of RSV Fusion Glycoprotein Trimer Bound to a Prefusion-Specific Neutralizing Antibody", Science Express, vol. 340, No. 6136, Apr. 25, 2013, 8 pages.
Tan et al., "Human Respiratory Syncytial Virus Isolate 08-046972, Complete Genome", GenBank Accession No. JX015498, available online at <http://www.ncbi.nlm.nih.gov/nuccore/JX015498>, Dec. 2012, 6 pages.
Rigter et al., "A Protective and Safe Intranasal RSV Vaccine Based on a Recombinant Prefusion-Like Form of the F Protein Bound to Bacterium-Like Particles", PLOS One, vol. 8, No. 8, Aug. 2013, pp. 1-14.

* cited by examiner

Asterisks indicate approximate location of epitopes recognized by indicated antibodies

HEAT-STABLE RESPIRATORY SYNCYTIAL VIRUS F PROTEIN OLIGOMERS AND THEIR USE IN IMMUNOLOGICAL COMPOSITIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The invention relates to the field of medicine and in particular to vaccines, and, more particularly, recombinant proteins that are useful in vaccines to immunize against Respiratory Syncytial Virus (RSV).

BACKGROUND OF THE INVENTION

Human Respiratory Syncytial Virus (hRSV) causes acute upper and lower respiratory tract infections and is a major cause for hospitalization of infants in the first year of life. Re-infection with RSV occurs frequently and sterilizing immunity is never firmly established. RSV also causes a significant disease burden and mortality in the elderly, comparable to influenza.

hRSV is an enveloped negative strand RNA virus belonging to the subfamily Pneumovirinae of the family Paramyxoviridae. Other members of this subfamily are bovine RSV (bRSV) and human metapneumovirus (hMPV). The hRSV particle contains two major glycoproteins, which are the key targets of neutralizing antibodies: the attachment protein G and the fusion protein F (review by Collins P L and J A Melero. 2011. Progress in understanding and controlling respiratory syncytial virus: still crazy after all these years. Virus Res 162:80-99). There are two RSV serotypes (A and B), which differ more in their G than F proteins. The F protein appears to be a more efficient neutralizing and protective antigen compared to G. This may be related to the high carbohydrate content of the G protein, which may shield the protein from immune recognition. In addition, the G protein is also secreted from infected cells, in which form it may function as an antigen decoy. The F protein not only functions to fuse viral and host membranes, but also plays a major role in virus-cell attachment. Neutralizing antibodies targeting F may therefore interfere with virus-cell attachment and/or with virus-cell fusion.

The RSV F protein is a type I membrane protein that is synthesized as an inactive precursor protein (named 'F0') that assembles into trimers. This precursor protein is cleaved by furin-like proteases into the forms named 'F2', 'p27' and 'F1' during its transport through the secretory route. Homotrimers of F2 and F1, which are covalently linked via disulfide bridges, form the metastable pre-fusion active structure. The F1 contains heptad repeats A and B (referred to as HRA and HRB), the fusion peptide (FP) and the transmembrane (TM) domain, the latter two positioned at opposite sides of the molecule. Upon virus-cell attachment, conformational changes in the RSV F protein lead to the insertion of the hydrophobic fusion peptide into a host cell membrane. Subsequently, this fusion intermediate refolds into a highly stable post-fusion structure. The assembly of this latter structure is dictated by the assembly of a six-helix bundle (6HB). This 6HB contains HRA and HRB of each monomer in an anti-parallel conformation, as a result of which the transmembrane domain, located downstream of HRB, and the fusion peptide, located upstream of HRA, are positioned in adjacent positions and fusion of the viral and host membranes is achieved. Recent studies have elucidated the structure of the F protein in its post-fusion conformation (McLellan J S et al. 2011. J Virol 85:7788-96; Swanson K A et al. 2011. Proc Natl Acad Sci USA 108:9619-24).

hRSV vaccine development has been haunted by the disastrous results obtained with the formalin-inactivated virus vaccine that was tested in the 1960s. Disease severity and hospital admission rates were increased in vaccinated children, who were naturally infected with RSV later, and several deaths occurred. The mechanism of this vaccine-induced disease enhancement remains incompletely understood, but appears associated with low induction of neutralizing antibodies and recruitment of eosinophils. Next to this effort, a large number of RSV vaccine strategies has been explored with varying success, including live attenuated RSV strains, subunit vaccines and viral vectored vaccines (Groothuis J R et al. 2011. Prevention of serious respiratory syncytial virus-related illness. I: Disease pathogenesis and early attempts at prevention. Adv Ther 28:91-109; Hurwitz J L. 2011. Respiratory syncytial virus vaccine development. Expert Rev Vaccines 10:1415-33). Obviously, successful RSV vaccines should induce protective immunity, but no immunopathology.

REPORTED DEVELOPMENTS

Currently, the only available option to prevent RSV-mediated disease is the passive administration of the commercially available RSV neutralizing monoclonal antibody Palivizumab. This product is used as prophylaxis for RSV infection and recognizes a highly conserved epitope in the F protein (Beeler J A and K van Wyke Coelingh. 1989. Neutralization epitopes of the F glycoprotein of respiratory syncytial virus: effect of mutation upon fusion function. J Virol 63:2941-50; Groothuis J R et al. 2011. Prevention of serious respiratory syncytial virus-related illness. II: Immunoprophylaxis. Adv Ther 28:110-25). However, due to its high cost the use of Palivizumab is restricted to infants considered at high risk of developing severe respiratory disease.

Although there is a need for a vaccine for protection of the general population, there is currently no approved vaccine against RSV available. Many vaccine candidates based on the main RSV neutralizing antigen, which is the F protein, failed due to problems with stability, reproducibility and potency.

Although the post-fusion form of RSV F was shown to contain neutralizing epitopes (McLellan J S et al. 2011. Structure of respiratory syncytial virus fusion glycoprotein in the postfusion conformation reveals preservation of neutralizing epitopes. J Virol 85:7788-96; Swanson K A et al. 2011. Structural basis for immunization with postfusion respiratory syncytial virus fusion F glycoprotein (RSV F) to elicit high neutralizing antibody titers. Proc Natl Acad Sci USA 108:9619-24) Magro and coworkers showed that antibodies specific for the pre-fusion form of F account for most of the neutralizing activity found in human sera (Magro M et al. 2012. Neutralizing antibodies against the preactive form of respiratory syncytial virus fusion protein offer unique possibilities for clinical intervention. Proc Natl Acad Sci USA 109:3089-94). Furthermore, RSV neutralizing antibodies were identified that recognize F, but that do not recognize recombinant soluble ectodomains thereof that are presumably in the post-fusion conformation (WO 2008/147196; US 2012/0070446; McLellan J S et al. 2011. J Virol 85:7788-96; Swanson K A et al. 2011. Proc Natl Acad Sci USA 108:9619-24; Gonzalez-Reyes L et al. 2001. Cleavage of the human respiratory syncytial virus fusion protein at two distinct sites is required for activation of membrane fusion. Proc Natl Acad Sci USA 98:9859-64; Ruiz-Arguello M B et al. 2002. Effect of proteolytic processing at two distinct sites on shape and aggregation of an anchorless fusion protein of human respiratory syncytial virus and fate of the intervening segment. Virology 298:317-26; Ruiz-Arguello M B et al. 2004. Thermostability of the human respiratory syncytial virus fusion protein before and after activation: implications for the membrane fusion mechanism. J Gen Virol 85:3677-87), see FIG. 2. These antibodies, which presumably recognize pre-fusion F or an intermediate form between pre- and post-fusion F, and not post-fusion F, were shown to more effectively neutralize RSV than Palivizumab, which recognizes all forms of F protein.

Attempts to modify the RSV F protein for use in an immunological composition have been reported (WO2010/149743; WO2012/158613).

BRIEF DESCRIPTION OF THE DRAWINGS

The patent or application file contains at least one drawing executed in color. Copies of this patent or patent application publication with color drawing(s) will be provided by the USPTO upon request and payment of the necessary fee.

FIG. 12A shows that, in the pre-fusion state where 6HB is not present, the epitope for AM22 is available, while the epitope for 131-2a is shielded.

SUMMARY OF THE INVENTION

Figure 1:
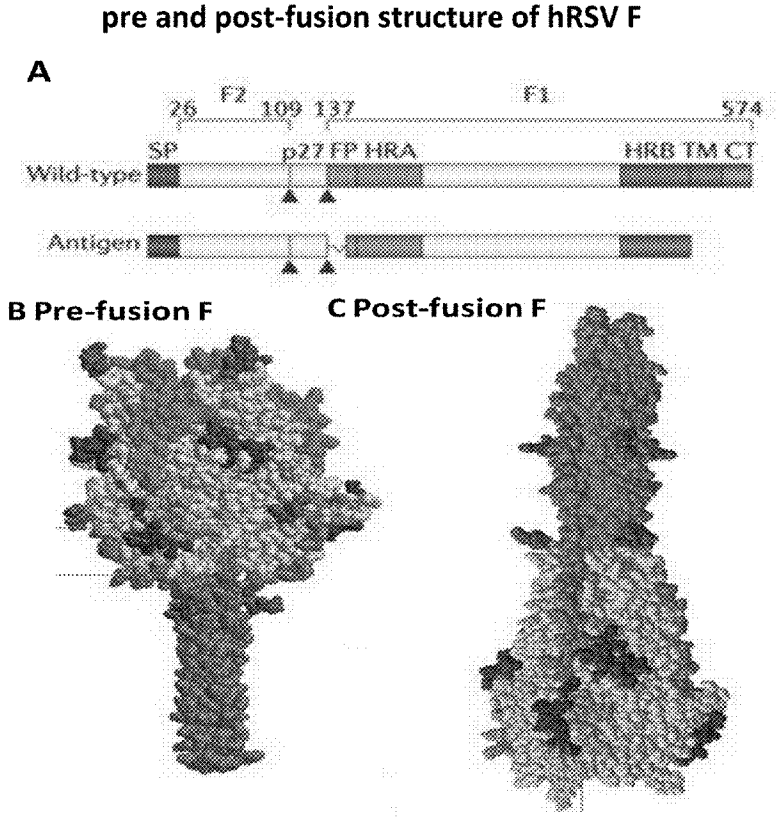
FIG. 1 shows (a) a comparison of wild-type fusion (F) protein from respiratory syncytial virus (RSV) with an engineered RSV F antigen. Arrowheads indicate furin cleavage sites, and the peptide p27 is released after cleavage. The F1 and F2 fragments of the wild-type sequence, which are produced as a result of furin cleavage, are indicated. Panel (b) is a model of the engineered RSV pre-fusion F, based on data from parainfluenza virus 5 (PIV-5) pre-fusion F and engineered RSV post-fusion F crystal structures. Panel (c) displays the engineered RSV post-fusion F structure of (a). CT=cytoplasmic tail; SP=signal peptide; TM=transmembrane region. (Taken from Nature Reviews Microbiology 10, 807-813; December 2012)
Figure 2:
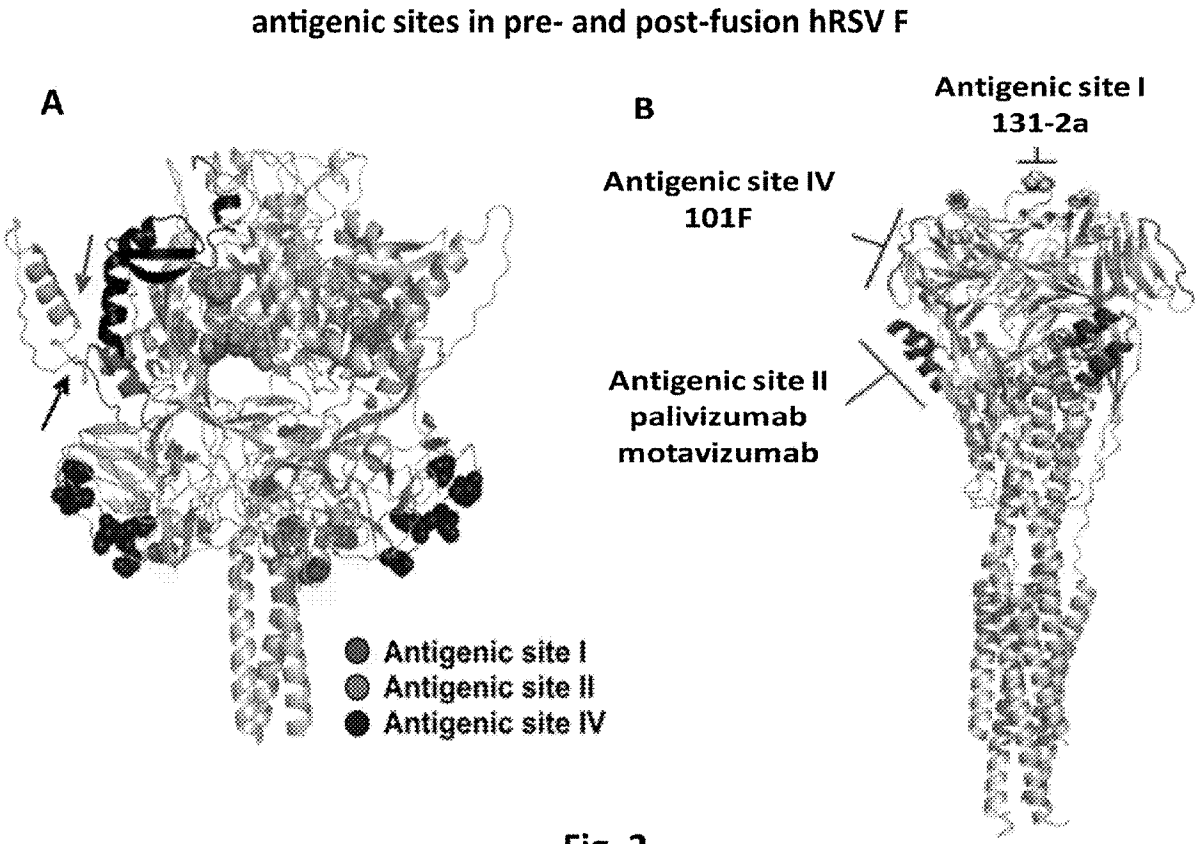
FIG. 2 (Taken from J. Virol. August 2011 vol. 85 no. 15 7788-7796) shows in panel (A) a three-dimensional model of the proposed pre-fusion conformation of the hRSV F trimer, built using the SWISS-MODEL server facilities (see the website found at swissmodel.expasy.org) and the atomic coordinates of the pre-fusion structure of the PIVS F protein (Protein Data Bank code, 2B9B) as a template. The backbone structure of the three monomers is shown in gray. Fusion peptide sequences of one monomer are shown in pink, and those of HRA are shown in black. Residues that are changed in virus isolates or in escape mutants selected with monoclonal antibodies, whose epitopes map in different antigenic sites of the F protein, are shown as colored spheres (antigenic site I, amino acid 389; antigenic site II, amino acids 262, 268, 272, and 275; and antigenic site IV, amino acids 429, 432, 433, 436, and 447). The two proteolytic cleavage sites are indicated with arrows in one of the monomers. Panel (B) shows the neutralizing epitopes on RSV F with a deleted FP. Epitopes for motavizumab and palivizumab (antigenic site II), 101F (antigenic site IV), and 131-2a (antigenic site I) are solvent exposed and in conformations compatible with antibody binding. Residues 254 to 277 are colored red (antigenic site II), residues 429 to 437 are colored blue (antigenic site IV), and atoms in Pro389 are shown as spheres (antigenic site I) (residue numbering according to J. Virol. August 2011 vol. 85 no. 15 7788-7796).

The present invention relates to a heat-stable oligomeric complex of a recombinant polypeptide presenting at least one antigenic epitope of the pre-fusion Respiratory Syncytial Virus (RSV) F protein, said polypeptide comprising the RSV F protein ectodomain from which the HRB region is functionally deleted and from which the transmembrane and cytoplasmic domains are deleted and replaced with a heterologous trimerization domain, and wherein the two multi-basic furin cleavage sites in said ectodomain are deleted or mutated, thereby rendering said sites defective. The invention further relates to an immunogenic composition comprising the aforesaid heat-stable oligomeric recombinant polypeptide and a method of inducing an immune response in a subject to RSV F comprising administering to said subject said immunogenic composition.

DETAILED DESCRIPTION

The design and evaluation of recombinant soluble F proteins of RSV has suffered considerably by a lack of tools to demonstrate the conformational status of a recombinant F protein. Based on the available literature the inventors of the present invention hypothesized that the post-fusion form of F should comprise a stable 6HB and that it should be recognized by post-fusion specific antibodies, but not by pre-fusion specific antibodies. In contrast, the pre-fusion form of the F protein should not carry the 6HB, will be recognized by pre-fusion specific antibodies, but not by post-fusion specific antibodies. Using this knowledge, it was reasoned that such pre-fusion specific antibodies would enable the identification of RSV F protein mutants that are stable (resistant to for instance heat) and remain in their pre-fusion conformation also under stressful conditions. Such stable pre-fusion mutants could in a next step be used in vaccines against RSV because they would—in their stable—conformation give an immune response (in vivo) and give rise to neutralizing antibodies that would be able to neutralize the virus carrying pre-fusion state F proteins. The present invention discloses that the inventors were indeed able to identify a recombinant RSV F protein mutant that is stably maintained in its pre-fusion conformation and is therefore useful in RSV vaccines.

The present invention may be understood with reference to the following definitions.

'Functionally deleted' means a deletion of a sequence of amino acids (which may be referred to as a 'domain') from a natural protein sequence such that the function of the deleted domain is lost, and the properties of the protein are thereby altered.

'Heat-stable' means that a polypeptide retains its three dimensional conformation in aqueous solution over a range of temperatures, and thereby retains its properties, including for example such polypeptide's antigenic properties. Preferred temperature ranges are from about 5 degrees C. to about 60 degrees C. A more preferred range is from about 10 degrees C. to about 80 degrees C. A most preferred range is from about 20 degrees C. to about 100 degrees C. Exemplary conformations are those characterized as a pre-fusion state.

"Oligomer" or 'oligomeric complex' means polypeptide that consists of two, three, or four polypeptide monomers, such as a dimeric, trimeric or tetrameric complexes of essentially the same polypeptide monomers. Most preferred oligomeric polypeptides according to the present invention are trimeric polypeptides.

'Post-fusion conformation' or 'post-fusion state' means a three-dimensional protein configuration that differs from that configuration taken by the polypeptide or polypeptide oligomer upon initial expression or oligomeric assembly, and results from the interaction of such polypeptide or oligomer from enzymatic action and/or physical contact with other proteins or proteinaceous assemblies, such as a cell membrane. The RSV F proteins that form a post-fusion state are RSV F proteins that include an HRA-HRB 6HB.

'Pre-fusion conformation' or 'pre-fusion state' means a three-dimensional protein configuration taken by the polypeptide or polypeptide oligomer upon initial expression or oligomeric assembly. RSV F proteins form RSV F protein oligomers that exhibit a pre-fusion configuration prior to fusing with the cell membrane. Pre-fusion RSV F proteins include the following characteristics: the HRA region is packed against domain III in the RSV F head region and/or the HRB region forms a trimer coil-coil stalk in proximity to domains I and II rather than associating with the HRA region in the context of the 6-helix bundle (6HB).

'Purified' protein or polypeptide means a protein or polypeptide isolated from other components of the polypeptide production system such that the amount of protein relative to other macromolecular components present in a composition is substantially higher than that present in a crude preparation. In general, a purified protein or polypeptide will be at least about 50% homogeneous and more preferably at least about 75%, at least about 80%, at least about 90%, at least about 95% or substantially homogeneous.

The RSV F ectodomain protein sequence is exemplified by the sequence of SEQ ID NO: 18. References to the sequence numbering and identifiable domains of the RSV F protein will herein be made to SEQ ID NO: 18. However, other strains of RSV may also be used to generate equivalent recombinant polypeptides.

The present invention relates to recombinant soluble proteins that mimic the pre-fusion state of human RSV F protein. See FIG. 1 for an image depicting the pre-fusion and the post-fusion conformation of the RSV F protein. The higher order modified RSV F protein structures found to be heat-stable, as disclosed herein, are oligomers of the polypeptide, and most likely, the polypeptide trimers of the modified RSV F polypeptide. The present polypeptide is likely formed into a trimer configuration based on size as detected in the experiments disclosed herein and because a trimerization motif is present in the modified polypeptide construct.

Preferably, the heat-stable oligomeric polypeptide according to the present invention is stable at room temperature. More preferably, the polypeptide is stable at temperatures up to 40° C., and even more preferably, the polypeptide is stable at temperatures up to 60° C., and yet in an even more preferred embodiment, the heat-stable recombinant polypeptide of the invention is stable at temperatures up to 70° C. In a most preferred aspect, the heat-stable recombinant polypeptide according to the present invention remains stable at temperatures of about 96° C. for at least about 5 to about 15 minutes.

The heat-stable recombinant polypeptide according to the invention comprises a functional deletion of the HRB region. This is different from what has been performed in the art and as shown herein, for instance by introducing (cysteine or alanine) mutations in the HRB region (WO 2012/158613). Such mutants cannot—similar to what has been shown intra—form 6HB structures, but still result in labile conformations. Such labile conformations are prevented by removing the HRB region from the RSV F protein as disclosed herein. The polypeptide of the present invention has a functional deletion of the HRB region of the RSV F protein such that the HRB region can no longer perform its natural function, for instance in building the 6-helix bundle (6HB) rendering the protein unable to form a post-fusion conformation. The deletion of the HRB region preferably comprises the amino acids of SEQ ID NO: 10. It will be appreciated by the person skilled in the art that such deletion may be slightly smaller and/or slightly bigger on either side of the HRB region, and/or may be shifted by a small number of amino acids. Nonetheless, such deletions will still render a functional deletion of the HRB region and, in combination with the mutations of the furin cleavage sites and the addition of a heterologous trimerization motif, provide a heat-stable polypeptide as shown herein.

The furin cleavage sites of the RSV protein may be mutated by different methods known in the art, for instance by replacement of the arginine residues by any other type of amino acid, or by deletions of the crucial residues. In a preferred embodiment, the mutation of the furin cleavage sites comprises the replacement of all arginine residues with lysine residues.

The heat-stable oligomeric polypeptide of the invention comprises a heterologous trimerization domain selected from the group consisting of: GCN4 leucine zipper trimerization motif, the trimerization motif from influenza virus HA protein, SARS spike, HIV gp41, NadA, ATCase and foldon sequence. In a preferred embodiment, said heterologous trimerization domain is a GCN4 leucine zipper trimerization motif. Leucine zipper motifs such as GCN4, as well as other trimerization motifs, induce the formation of trimeric-coiled coils, in which three alpha-helices are coiled together like the strands of a rope. Such trimerization motifs have been used in the art to generate RSV vaccines based on RSV F proteins (WO 2010/149743 and WO 2012/158613).

The heat-stable oligomeric polypeptide according to the invention is preferably recognized by the pre-fusion specific monoclonal antibodies AM22 and D25, the preparation and characteristics of which are both described in WO2008/147196, the recognition indicating that pre-fusion specific antigenic epitopes are available.

The polypeptides of the present invention are suitable as antigenic component(s) of a vaccine that protects against infection and disease caused by human RSV (serotype A and B). By employing the present F protein mutation/deletion strategy to F proteins of other viruses belonging to the sub-family Pneumovirinae, immunogenic polypeptides protective against infection caused by these similar viruses, such as bovine RSV or human metapneumovirus, may be prepared.

The invention further relates to an immunogenic composition that is an effective vaccine to immunize against RSV infections. In a preferred embodiment, said immunogenic composition comprises an adjuvant to boost immunogenicity. In yet another aspect, the invention relates to a recombinant expression vector comprising a nucleotide sequence encoding the heat-stable polypeptide according to the invention.

The recombinant proteins of the present invention may also be used in diagnostics assays, with which one may measure the antibody response specifically targeted against the pre-fusion form of the F protein of RSV (or relatives thereof). This response may be of predictive value with respect to disease. Furthermore, the recombinant proteins of the present invention may be used to test the quality of the antibody response induced by a candidate vaccine, and may be used to generate conformation-specific antibodies which may be used as therapeutics, to study the epitopes present on a candidate vaccine, or to control the antigenicity of a (candidate) vaccine.

In another preferred embodiment, the invention relates to a heat-stable oligomeric complex of a recombinant polypeptide according to the invention that further comprises a LysM peptidoglycan binding domain as a tag. For easy purification and detection of the recombinant polypeptide, the polypeptide preferably comprises a triple Strep-tag. In yet another preferred aspect, the ectodomain within the polypeptide is a soluble ectodomain.

The heat-stable oligomeric complex of a recombinant polypeptide of the present invention is in a pre-fusion conformation that is antigenic, and can be confirmed by the use of antibodies that neutralize and recognize certain epitopes in the RSV F protein. In a preferred aspect, the heat-stable recombinant polypeptide according to the invention comprises an available epitope that is recognized by monoclonal antibody AM22. Whether AM22 recognizes the polypeptide can be easily checked by common methods used in the art, and as disclosed herein.

The present invention is useful in the field of medicine, and in particular in the field of vaccines against RSV infections. The heat-stable polypeptides of the present invention can be used in immunogenic compositions that may be applied in vaccination programs, in regions that present storage and handling challenges such as the third world, to protect (human) subjects who are at risk of developing disease caused by RSV.

Because the polypeptides of the present invention are stable in their pre-fusion conformation, presenting pre-fusion specific epitopes recognized by potent neutralizing antibodies, epitopes absent in polypeptides folded in the post-fusion conformation, the polypeptides are capable of inducing superior pre-fusion specific neutralizing antibodies that protect against RSV infection. The importance of pre-fusion-specific VN antibodies in naturally RSV infected humans has been demonstrated by Magro Metal. (2012. Neutralizing antibodies against the preactive form of respiratory syncytial virus fusion protein offer unique possibilities for clinical intervention. Proc Natl Acad Sci USA 109:3089-94). Hence, the present invention also relates to an immunogenic composition comprising the purified heat-stable oligomeric polypeptide of the present invention, and optionally further comprises excipients commonly used in vaccine preparations.

It should be understood that the present polypeptides used in the immunogenic compositions of the present invention do not include the signal peptide, which is co-expressed with the heat-stable polypeptide, but which is cleaved from the polypeptide before leaving the production cell. In a preferred aspect, although not strictly necessary, the additional (non-RSV F protein) tag sequences are removed by enzymatic digestion during or after the purification process. Preferably, an immunogenic composition according to the present invention further comprises an adjuvant to further boost the immune response.

The present invention also relates to recombinant expression vectors comprising the nucleotide sequences encoding the heat-stable polypeptides of the present invention. Moreover, the invention relates to a method of inducing an immune response in a subject to RSV F comprising administering to said subject an immunogenic composition according to the invention, and to methods of vaccinating human subjects against RSV infections by applying the immunogenic compositions as disclosed herein. The invention also relates to the use of a heat-stable polypeptide according to the invention for the manufacture of a medicament for the prophylaxis or treatments of RSV infections or diseases that follow an RSV infection. The invention further relates to heat-stable recombinant polypeptides and/or recombinant expression vectors according to the invention for use in vaccines against RSV infections.

Immunogenic compositions according to the present invention may be prepared, tested for immunogenicity, efficacy and safety employing the technology disclosed in published PCT application WO2012/128628, hereby incorporated by reference. Vaccine formulations may be based on particles derived from inactivated Lactococcus lactis bacteria, a safe bacterium traditionally used in the food industry, such as for the production of cheese (described elsewhere as Gram-positive Enhancer Matrix or Bacterium-Like Particles and herein referred to as "BLPs"). BLPs are obtained by the acidic heat treatment of L. lactis bacteria, resulting in non-living spherical particles that predominantly consist of a peptidoglycan surface, the preparation of BLPs is disclosed in WO 02/101026. The antigenic polypeptides of the present invention may be loaded onto the BLPs, which employs the non-covalent coupling technology referred to as, Protan technology, disclosed in U.S. Pat. No. 7,312,311, which is hereby incorporated by reference. The resulting antigen-associated BLPs constitute the final vaccine that may be delivered to humans via the mucosal layers of the nose (e.g. drops or spray) or mouth (e.g. capsule, tablet or liquid), without the need for an injection.

EXAMPLES

Example 1

RSV F Protein Preparations

This example describes the generation of different F protein constructs and their characterization with respect to antibody binding and gel electrophoretic mobility. This analysis demonstrates that the tools and assays are suitable to demonstrate the conformational state of a RSV F protein. Also, a method is disclosed that shows the production of recombinant soluble proteins that mimic the pre-fusion state of human RSV F.

Figure 3:
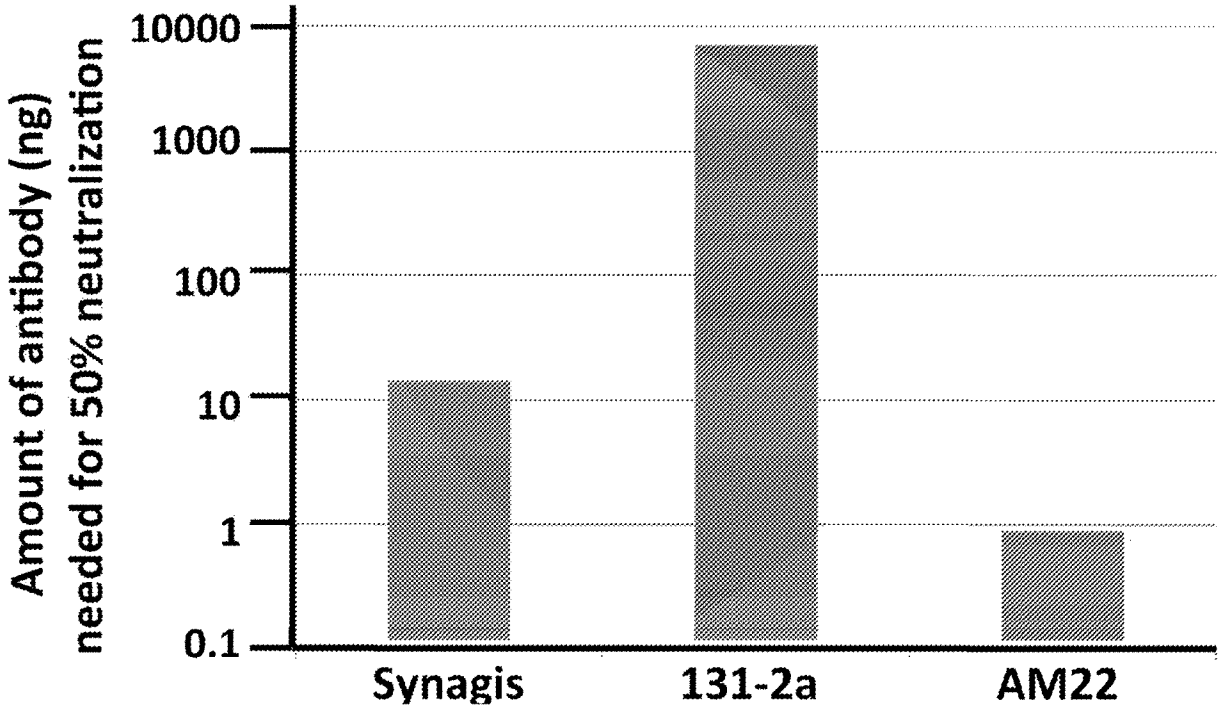
FIG. 3 shows the amount of antibody needed to block 50% infection in a microneutralization assay. The lower the amount, the more effective the antibody. Synagis®=Palivizumab FIG. 4 provides a schematic representation of the different constructs used in the present invention. TM=transmembrane region; CT=cytoplasmic tail; CD5=signal peptide; HRA=heptad repeat A; HRB=heptad repeat B; GCN=GCN4 trimerization motif.

In an initial step, a comparative analysis of the virus neutralizing capacity was performed of the MAbs that were used herein (FIG. 3). In agreement with previous studies, antibody 131-2a hardly demonstrated any neutralizing capacity compared to Palivizumab or AM22 (McLellan J S et al. 2011. J Virol 85:7788-96). In contrast, AM22 efficiently neutralized infection with hRSV and was even more potent than Palivizumab, in agreement with what was shown in US 2012/0070446. Palivizumab was shown to recognize the post-fusion form of hRSV F, but it likely also recognizes the pre-fusion form of F, because its epitope appears also to be present in the pre-fusion form based on the X-ray structure solved for parainfluenza virus 5 F protein (Yin H S et al. 2006. Structure of the parainfluenza virus 5 F protein in its metastable, pre-fusion conformation. Nature 439:38-44). Antibody 131-2a recognizes an epitope that is probably not accessible for antibody binding in the pre-fusion form of F. The presumed inability of 131-2a to bind the pre-fusion form of RSV F corresponds with its lack of neutralizing activity. Finally, the epitope recognized by AM22 has not been identified yet.

The inventors of the present invention and others previously demonstrated that recombinant soluble class I fusion proteins can be stably maintained in their pre-fusion conformation by the addition of artificial trimerization domains (de Vries R P et al. 2010. The influenza A virus hemagglutinin glycosylation state affects receptor-binding specificity. Virology 403:17-25; Wei C J et al. 2008. Comparative efficacy of neutralizing antibodies elicited by recombinant hemagglutinin proteins from avian H5N1 influenza virus. J Virol 82:6200-8; Yang X et al. 2000. Characterization of stable, soluble trimers containing complete ectodomains of human immunodeficiency virus type 1 envelope glycoproteins. J Virol 74:5716-25; Yin H S et al. 2006. Nature 439:38-44). Use was made of a similar construct that was used previously to express recombinant soluble bioactive influenza A virus HA protein to express soluble F proteins (Cornelissen L A et al. 2010. A single immunization with soluble recombinant trimeric hemagglutinin protects chickens against highly pathogenic avian influenza virus H5N1. PLoS One 5:e10645; de Vries R P et al. 2011. Only two residues are responsible for the dramatic difference in receptor binding between swine and new pandemic H1 hemagglutinin. J Biol Chem 286:5868-75; de Vries R P et al. 2010. Virology 403:17-25).

In the expression constructs used in the present invention (overview provided in FIG. 4), the human codon-optimized RSV F ectodomain sequence of a European clinical isolate (Tan L et al. 2012. Genetic Variability among Complete Human Respiratory Syncytial Virus Subgroup A Genomes: Bridging Molecular Evolutionary Dynamics and Epidemiology. PLoS One 7:e51439) was preceded by a signal peptide-encoding sequence. The ectodomain sequence was optionally followed by a sequence coding for the GCN4 leucine zipper trimerization motif (Harbury P B et al. 1993. A switch between two-, three-, and four-stranded coiled coils in GCN4 leucine zipper mutants. Science 262:1401-7). The protein with the codon-optimized ectodomain sequence (which encodes the wild type version of this part of the protein), in which the wild type furin cleavage sites and the HRB domain are present, and wherein the ectodomain is followed by the GCN4 motif was referred to as Fwt-GCN. For comparison, the wild-type F protein-encoding gene was also cloned into vectors lacking the trimerization motif (referred to as Fwt). The tags consisted either of a triple Strep-tag for easy purification, or of a LysM peptidoglycan binding domain followed by the triple Strep tag as it turned out that, for yet unknown reasons, GCN-containing F constructs were expressed to higher levels when also the LysM domain was present. In addition to the wild-type constructs (Fwt and Fwt-GCN), expression vectors encoding F proteins with modified furin-cleavage sites were also constructed. These mutations are specified in the protein sequence of SEQ ID NO: 20, shown as R to K mutations in the $1^{st}$ furin cleavage site (positions 81, 83 and 84) and in the $2^{nd}$ furin cleavage site (positions 108, 110 and 111). The nucleotide sequences of these mutants are given in SEQ ID NO: 19. These cleavage site (arg->lys) mutant constructs are referred to as 'Flys'. Others showed that in the absence of furin cleavage the F protein is prevented to adopt the post-fusion conformation (Ruiz-Arguello M B et al. 2002. Virology 298:317-26; Ruiz-Arguello M B et al. 2004. J Gen Virol 85:3677-87). This is in line with the idea that cleavage of F is required for activation of membrane fusion.

Gene construction and cloning was performed as follows: Two variants of a cDNA clone corresponding to residues 26 to 515 of the F protein of a European isolate of RSV serotype A (Genbank accession number JX015498.1) were synthesized using human-preferred codons by GenScript USA Inc. While one cDNA clone encoded the wild type F protein ectodomain, the other clone encoded a F protein ectodomain in which the arginine residues in the two multibasic furin cleavage sites are mutated into lysines (RARR to KAKK and RKRR to KKKK). Each cDNA was cloned into the pCD5 expression vector for efficient expression in mammalian cells (de Vries R P et al. 2010. Virology 403:17-25). The pCD5 vector had been modified such that the F protein-encoding sequences were cloned in frame downstream of a DNA sequence coding for a CD5 signal peptide and when indicated upstream of sequences encoding the heterologous GCN4 isoleucine zipper trimerization motif and the specified tag. The tag either consisted of a triple Strep-tagII (IBA, Germany) or of a LysM peptidoglycan binding domain (van Roosmalen M L et al. 2006. Mucosal vaccine delivery of antigens tightly bound to an adjuvant particle made from food-grade bacteria. Methods 38:144-9; WO2012/128628) followed by a triple StreptagII. Two codon-optimized DNA fragments encoding the variable heavy and light chains of antibody AM22 (US 2012/0070446 A1) were synthesized by GenScript USA, Inc. and cloned in-frame into pCAGGS mammalian expression vectors containing human IgG1 heavy and light constant domains, respectively.

Expression of the F protein ectodomains was achieved by transient transfection as follows: pCD5 expression vectors containing RSV F ectodomain-encoding sequences were transfected into HEK293T cells using polyethyleneimine I (PEI) in a 1:5 w/w ratio (μg DNA: μg PEI). At 6 h post transfection, the transfection mixture was replaced by 293 SFMII expression medium (Invitrogen), supplemented with sodium bicarbonate (3.7 g/L), glucose (2.0 g/L), Primatone RL-UF (3.0 g/L), penicillin (100 units/ml), Streptomycin (100 μg/ml), glutaMAX (Gibco), and 1,5% dimethylsulfoxide. Tissue culture supernatants were harvested 5-6 days post transfection. F proteins were either purified using Strep-tactin Sepharose beads according to the manufacturer's instructions (IBA, Germany) for further analysis of the protein. The AM22 expression vectors were co-transfected at a 1:1 ratio into HEK293T cells similarly as described above. The cell culture media were clarified by centrifugation and the AM22 antibody was purified with protein A sepharose beads using standard conditions. The concentration of purified protein was determined by using a Nanodrop 1000 spectrophotometer (Isogen Life Sciences) according to the manufacturer's instructions.

Expression and secretion of recombinant proteins were confirmed by sodium dodecylsulfate (SDS)-polyacrylamide gel electrophoresis (PAGE; 10% NuPAGE BisTris, Invitrogen) followed by western blotting using anti-Strep-tag antibody conjugated with horse radish peroxidase (HRP) (StrepMAB-classic-HRP, IBA), Palivizumab (Synagis®, Abbott Laboratories) followed by HRP-conjugated anti-human IgG antibody (ITK Southern Biotech). This latter antibody was also used to confirm expression of recombinant antibody AM22. Prior to SDS-PAGE analysis, the samples were resuspended in Laemmli sample buffer (LSB) that either did or did not contain 5% 2-mercaptoethanol (Sigma), and when indicated heated at 96° C. for 5-15 minutes.

Figure 5:
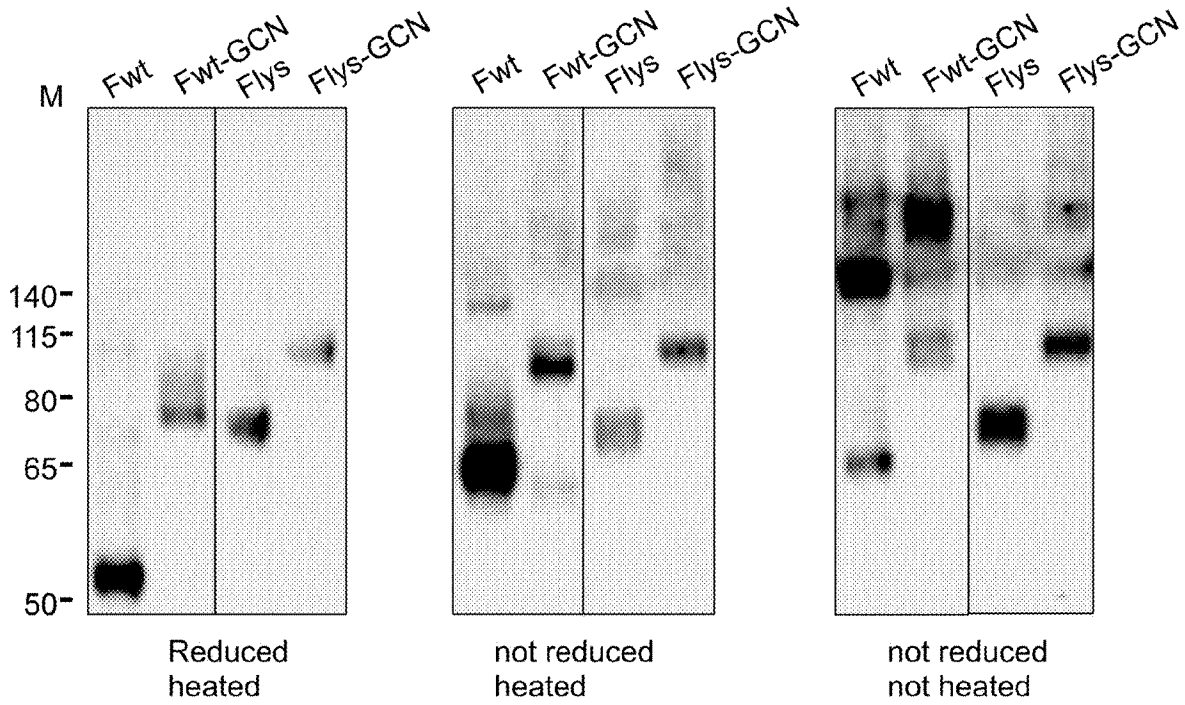
FIG. 5 shows western blots of Fwt, Fwt-GCN, Flys and Flys-GCN proteins that were either reduced and heated (left panel), not reduced and heated (middle panel) or not reduced and not heated (right panel). Higher order proteins in the right panel indicate the post-fusion state of these proteins that almost fully disappears upon treatment with 2-betamercaptoethanol (reducing) and heating prior to running the proteins on SDS-PAGE.

The results are given in FIG. 5. The epitope recognized by Palivizumab is located in the F1 part of the F protein. The results show that when the F ectodomains are subjected to SDS-PAGE under reducing conditions (i.e. in the presence of 2-mercaptoethanol), which results in separation of the otherwise disulfide-linked F1 and F2, they migrated with different electrophoretic mobilities corresponding to the absence or presence of the GCN-LysM sequences. Furthermore, the F proteins migrated at a higher position in the gel, when the furin-cleavage sites were mutated (compare Fwt with Flys, and Fwt-GCN with Flys-GCN) in agreement with these proteins not being cleaved. When the same F protein preparations were subjected to SDS-PAGE in the absence of reducing agents, the migration of the non-cleaved F proteins did not appear to be much affected.

In contrast, while the Fwt and Fwt-GCN proteins clearly ran at a lower position in the gel than the Flys and Flys-GCN under reducing conditions, the difference in the electrophoretic mobility appeared much smaller in the absence of reducing agents, in agreement with the F2 part still being attached to the F1 part via disulfide bridges also in the furin-cleaved proteins. The small difference in electrophoretic mobility between the cleaved and non-cleaved F proteins that was still noticeable is most likely explained by the dissociation of the glycosylated p27 sequence from the cleaved proteins. Interestingly, the electrophoretic mobility of the cleaved F proteins was dramatically changed when the preparations were not heated prior to electrophoresis under non-reducing conditions. In contrast to the non-cleaved proteins (Flys and Flys-GCN, the electrophoretic mobility of which was not much affected) the majority of the Fwt and Fwt-GCN proteins migrated at a much higher position in the gel. The migration of these latter proteins is explained by the cleaved F proteins adopting a stable post-fusion conformation, characterized by the presence of an extremely stable 6HB, resistant to SDS unless the protein preparations are heated. These results indicate that the large majority of the soluble, cleaved F ectodomains adopts a post-fusion conformation. The post-fusion conformation is not prevented when the ectodomain is extended with an artificial trimerization domain. However, the stable post-fusion conformation is not formed when the F proteins are not cleaved.

To confirm and extend these observations, a subsequent experiment was performed in which the purified F proteins were subjected to limiting proteolysis followed by SDS-PAGE under non-reducing conditions. Despite the fact that the furin-cleavage sites in Flys and Flys-GCN had been mutated by substitution of the arginines by lysines, these positions are still sensitive to trypsin digestion. Treatment of the Flys and Flys-GCN proteins with trypsin will thus result in cleavage of these proteins and possibly in formation of the SDS-resistant higher-order structure corresponding to the post-fusion conformation of the F protein.

Figure 6:
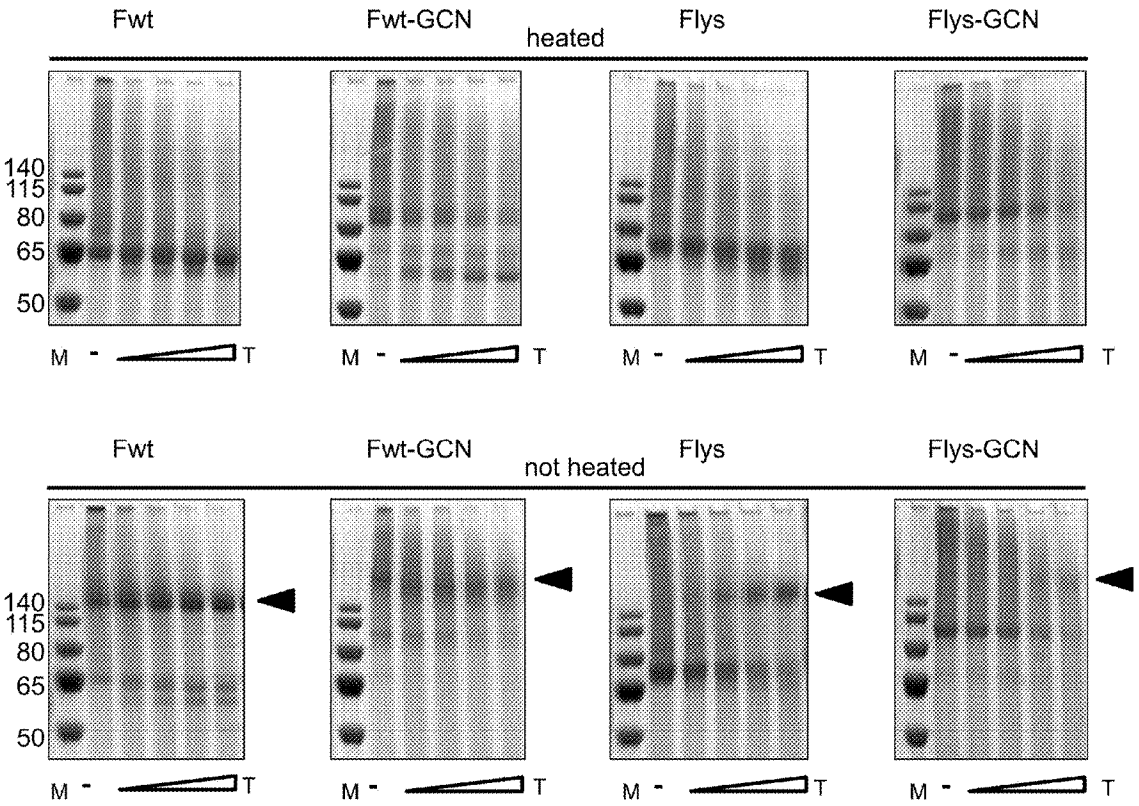
FIG. 6 shows a Coomassie Blue staining of gels on which Fwt, Fwt-GCN, Flys and Flys-GCN proteins were separated after heating (upper panels) or after no heating (lower panels) and increasing cleavage with trypsin (T).
Figure 7A:
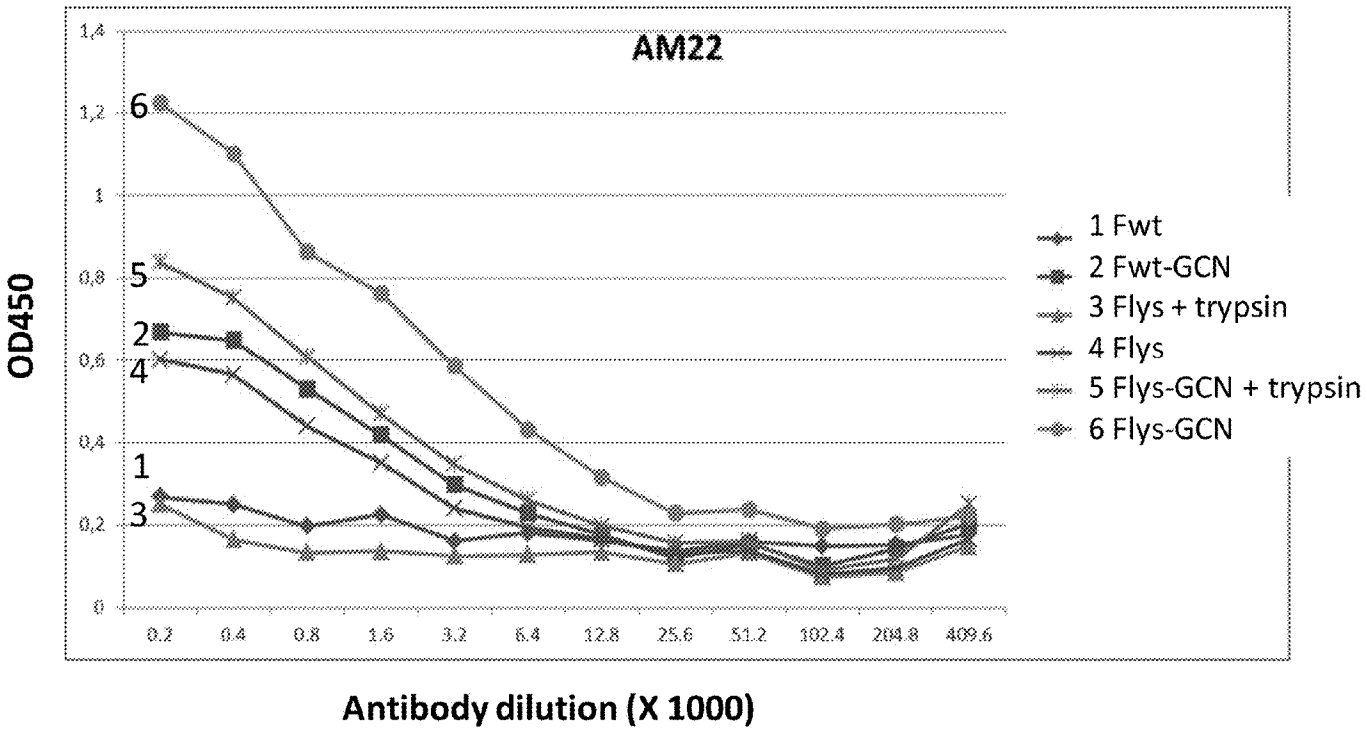
FIG. 7A shows the results of an ELISA assay with which the reactivity of different soluble F proteins (Fwt, Fwt-GCN, Flys and Flys-GCN) with the AM22 antibody was checked. The treatment with trypsin is indicated for Flys and Flys-GCN.
Figure 7B:
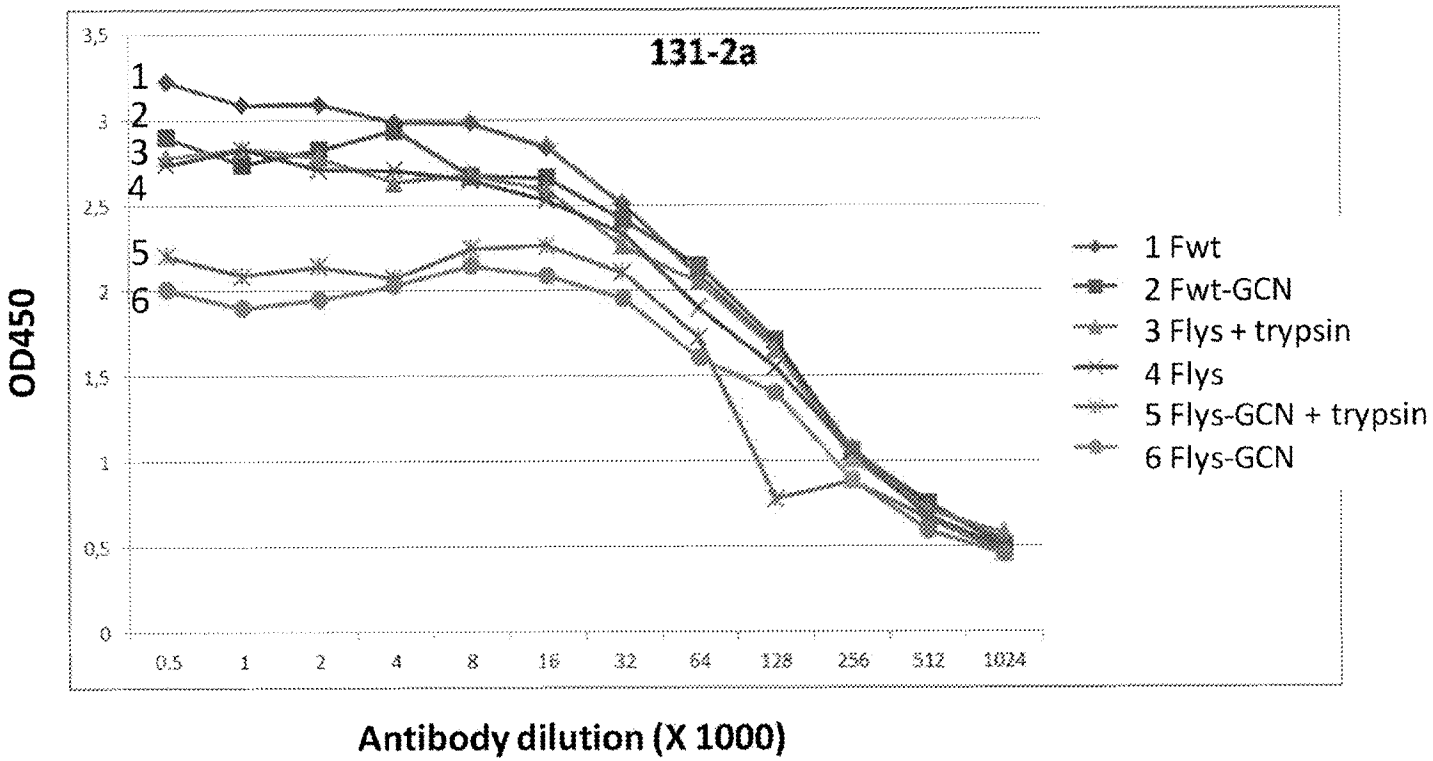
FIG. 7B shows the results of an ELISA assay with which the reactivity of different soluble F proteins (Fwt, Fwt-GCN, Flys and Flys-GCN) with the 131-2a antibody was checked. The treatment with trypsin is indicated for Flys and Flys-GCN.
Figure 7C:
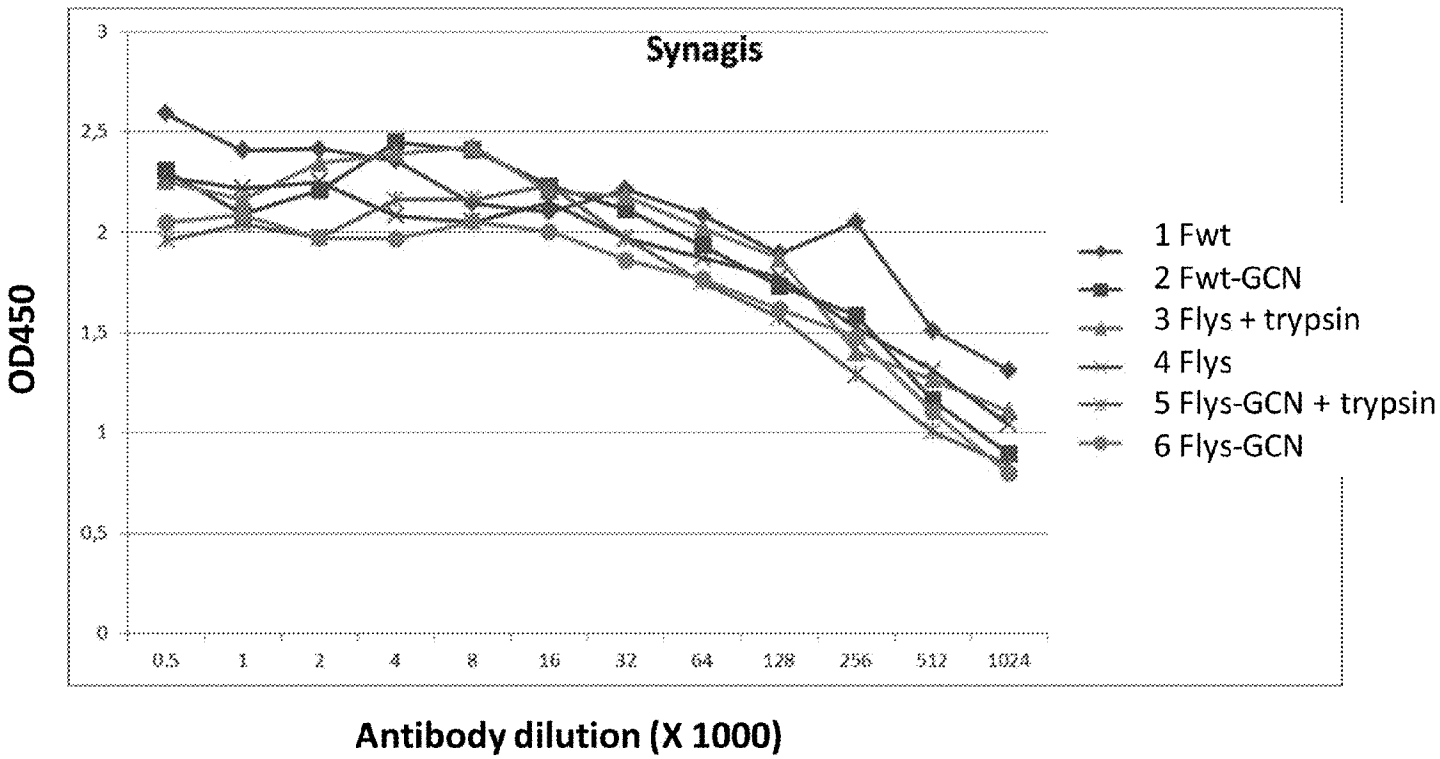
FIG. 7C shows the results of an ELISA assay with which the reactivity of different soluble F proteins (Fwt, Fwt-GCN, Flys and Flys-GCN) with the Synagis® (Palivizumab) antibody was checked. The treatment with trypsin is indicated for Flys and Flys-GCN.
Figure 7D:
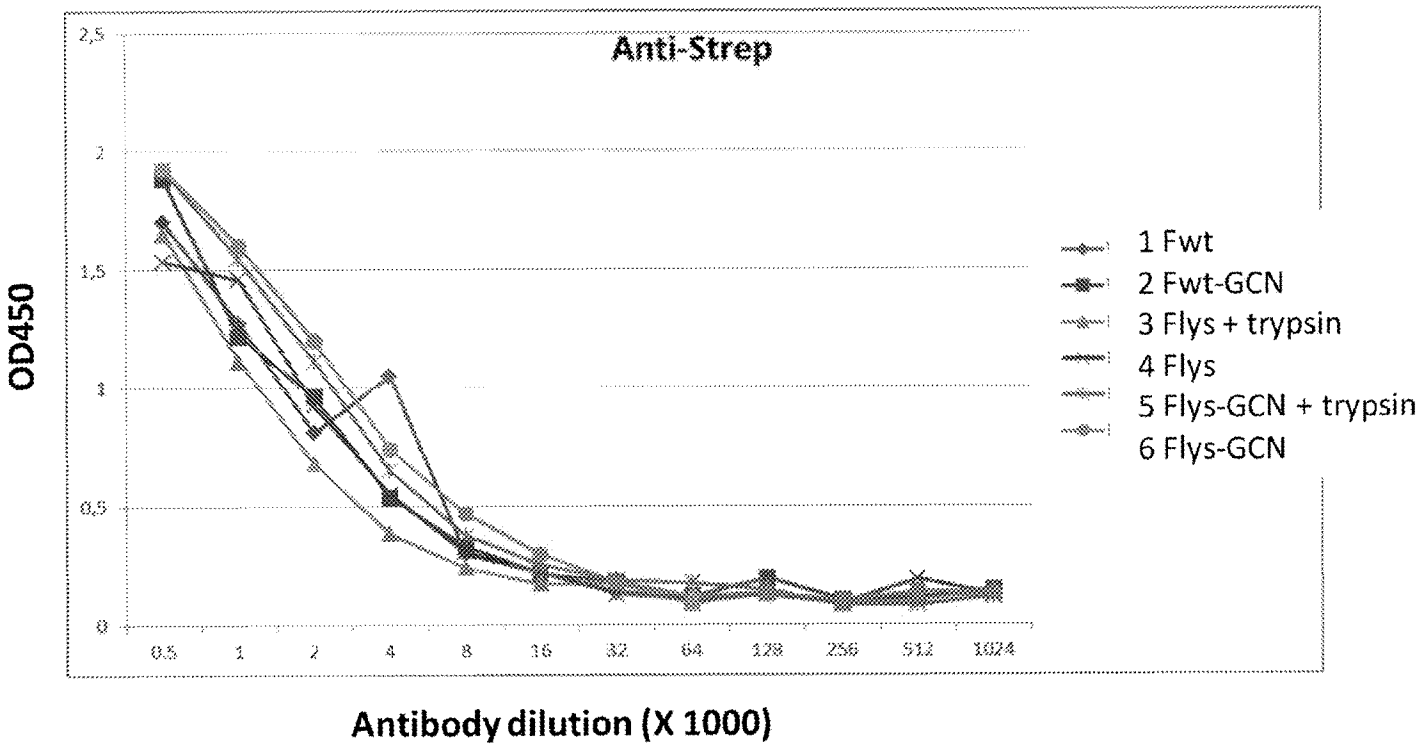
FIG. 7D shows the results of an ELISA assay with which the reactivity of different soluble F proteins (Fwt, Fwt-GCN, Flys and Flys-GCN) with the anti-strep antibody was checked. The treatment with trypsin is indicated for Flys and Flys-GCN.

Purified F proteins were (mock-) treated with varying amounts of TPCK treated trypsin from bovine pancreas (Sigma) for 30 min at 23° C. The samples were next put on ice and trypsin inhibitor (Sigma) was added, after which they were analyzed by SDS-PAGE as described above. Protein bands were visualized by general staining using the Colloidal Blue Staining kit (Invitrogen). The results are shown in FIG. 6. Clearly, digestion with trypsin indeed results in the appearance of the SDS-resistant higher-order structure corresponding to the post-fusion conformation of the F protein. Fwt and Fwt-GCN proteins were taken along as controls. The purified proteins were detected using Colloidal Coomassie Blue staining. Again Fwt and Fwt-GCN ran at their expected positions in the gel, when the samples were heated prior to electrophoresis (upper panels). When the samples were not heated, proteins ran at a much higher position in the gel (lower panels). As expected, treatment of these samples with trypsin did not affect the migration of the higher order structures much. However, trypsin treatment resulted to some extent in the removal of the F protein tags as demonstrated by the appearance of lower migrating F protein species when the samples were heated prior to electrophoresis. Treatment of the non-cleaved F proteins with trypsin resulted in the appearance of F proteins migrating at a much higher position in the gel under non-reducing conditions, similarly as observed for their Fwt and Fwt-GCN counterparts. The formation of the SDS-resistant higher-order structures was more apparent for Flys when compared to Flys-GCN, suggesting that the formation of the post-fusion conformation is prevented to some extend by the GCN trimerization motif.

The reactivity of the F protein preparations with the RSV F specific MAbs Palivizumab (Synagis®), AM22 and 131-2a were probed using an ELISA format. For this, 96-well Nunc maxisorp plates were overnight coated with different F protein preparations (50 ng per well) at 4° C. After blocking and extensive washing, the plates were incubated with limiting dilutions of Palivizumab (Synagis®, starting with 1 in 500 dilution of a 3 mg/ml stock), AM22 (starting with a 200 fold dilution of a 0.7 mg/ml stock), 131-2a (Millipore, starting with a 500 fold dilution of a 1 mg/ml stock), or anti-strep (StrepMAb classic from IBA, starting with a 500 fold dilution of the stock). After extensive washing, the plates were incubated with HRP conjugated goat-anti-human IgG antibodies (ITK Southern Biotech) or HRP conjugated rabbit-antimouse IgG antibodies (DAKO) at a 1:500 dilution for 1 h at RT. Detection of HRP reactivity was performed using tetramethylbenzidine substrate (BioFX) and a ELISA plate reader (EL-808 from Biotek). The results are given in FIG. 7.

All F proteins were coated with similar efficiencies as demonstrated by the binding of MAb specific for the Strep tag (Anti-Strep panel). Palivizumab displayed a concentration-dependent binding to all F protein preparations in agreement with the assumption that this antibody recognizes the F protein regardless of its conformational state. In contrast, AM22 was not able to bind Fwt, in agreement with the assumption that this antibody is not able to bind a protein in post-fusion conformation. However, intermediate binding was observed when the cleaved protein was extended with the trimerization motif (Fwt-GCN) or when cleavage was prevented (Flys). The highest reactivity was observed when these two features were combined (Flys-GCN). Trypsin treatment of Flys and Flys-GCN prior to coating of the wells resulted in reduced AM22 reactivity, which subsequently was comparable to the reactivity observed with Fwt and Fwt-GCN. Reactivity of Palivizumab with the F proteins was not affected by the trypsin treatment. MAb 131-2a efficiently bound to all F protein preparations.

These results show that binding of neutralizing antibody AM22 differs between different F protein preparations: Fwt, which adopts the post-fusion conformation, is hardly detected, while the highest reactivity was observed for Flys-GCN. From these results it was concluded that the majority of Fwt is in the post-fusion conformation (6HB+, 131-2a+, AM22−). Fwt-GCN is probably present in a mixture of conformations (6HB+, 131-2a+, AM22+/−). In the absence of cleavage, the F proteins do not adopt the post-fusion conformation (no 6HB). Their reactivity with both 131-2a and AM22 indicates that these non-cleaved proteins are in some form of intermediate state.

Example 2

Introduction of Cysteine Residues in the HRB Region

Figure 4:
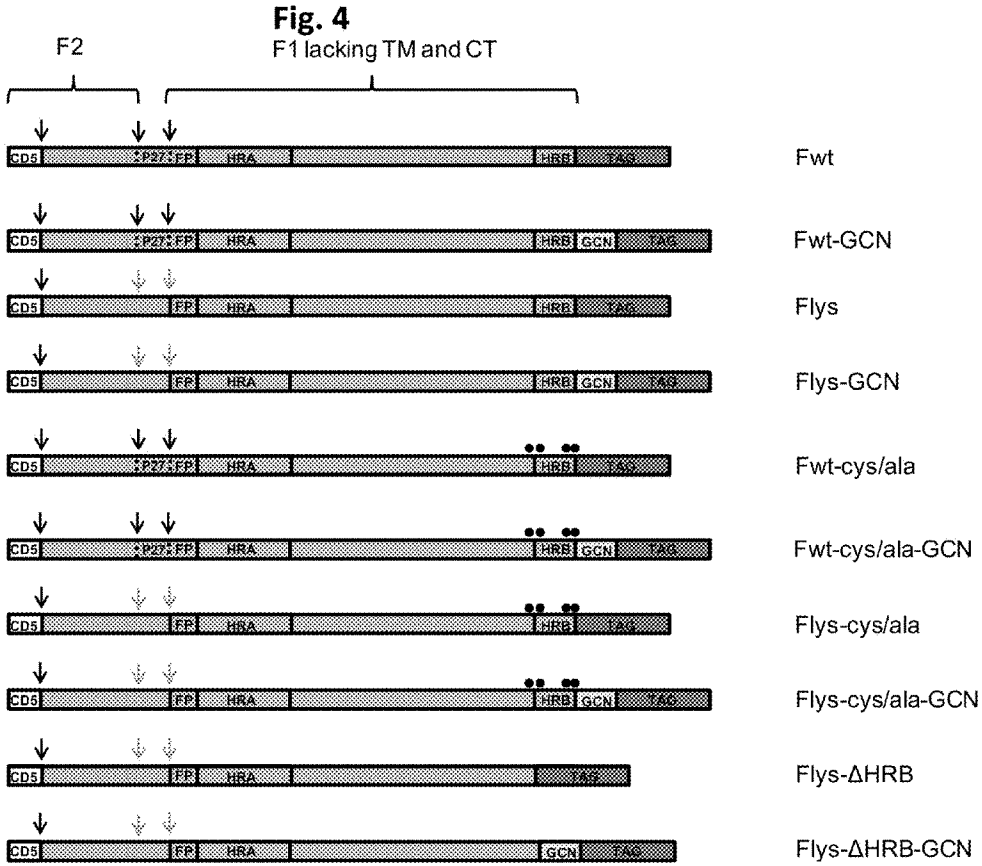
Figure 8:
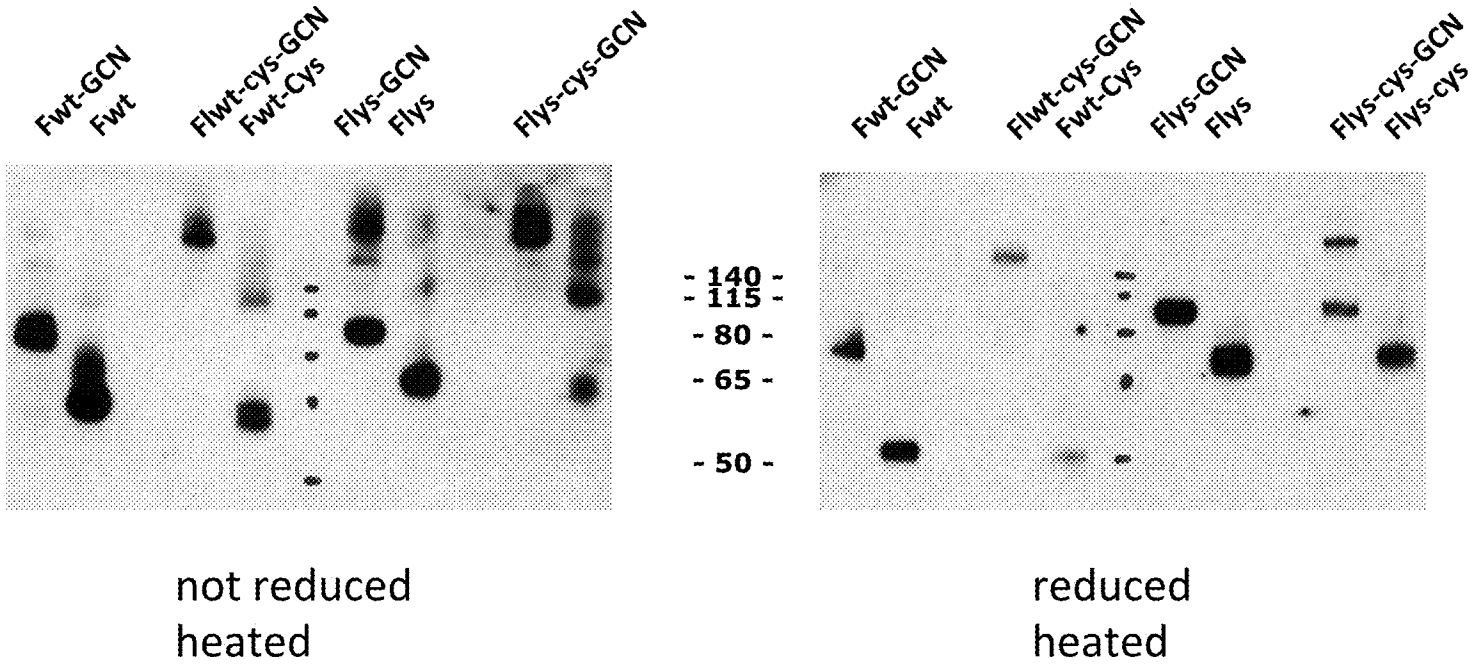
FIG. 8 shows a western blot of Fwt-GCN, Fwt, Fwt-cys-GCN, Fwt-cys, Flys-GCN, Flys, Flys-cys-GCN and Flys-cys proteins that were either heated but not reduced (left panel) or that were heated and reduced (right panel). The introduction of cysteines in the HRB domain as outlined in example 2 results in higher order structures that are resistant to heat and only partially sensitive to reduction.

Next, the characteristics of F proteins, in which 4 cysteine residues were introduced into their HRB domain (designated Fwt-cys; Fwt-cys-GCN; Flys-cys; Flys-cys-GCN; FIG. 4) were investigated. These cys substitutions, when introduced in a full length F protein (containing a transmembrane domain and cytoplasmic tail), were previously shown to result in intermolecular disulfide bridges which appeared to stabilize the F protein in its pre-fusion conformation (Magro M et al. 2012. Proc Natl Acad Sci USA 109:3089-94). Purified proteins were analyzed by SDS-PAGE in the absence or presence of reducing agents. As shown in FIG. 8, introducing the cysteine residues in HRB resulted in the formation of higher order structures, which could be observed on the non-reducing gel, even when the samples were heated. These higher order structures were most apparent for the F proteins with the GCN4 trimerization motif (Fwt-cys-GCN and Flys-cys-GCN), but also to some extent for the F proteins that lacked the GCN4 motif (Fwt-cys and Flys-cys). These higher order structures were not observed for the F proteins that contained a wild type HRB under these conditions, in agreement with the results shown in FIGS. 5 and 6. While the higher order structures of Fwt-cys and Flys-cys were sensitive to the presence of reducing agents (FIG. 8; right panel), this was much less so the case for the proteins that additionally contained the GCN4 motif. These data indicate the extreme stability of the higher order structures by introduction of the cysteine residues in HRB when also the GCN4 motif is present.

Figure 9:
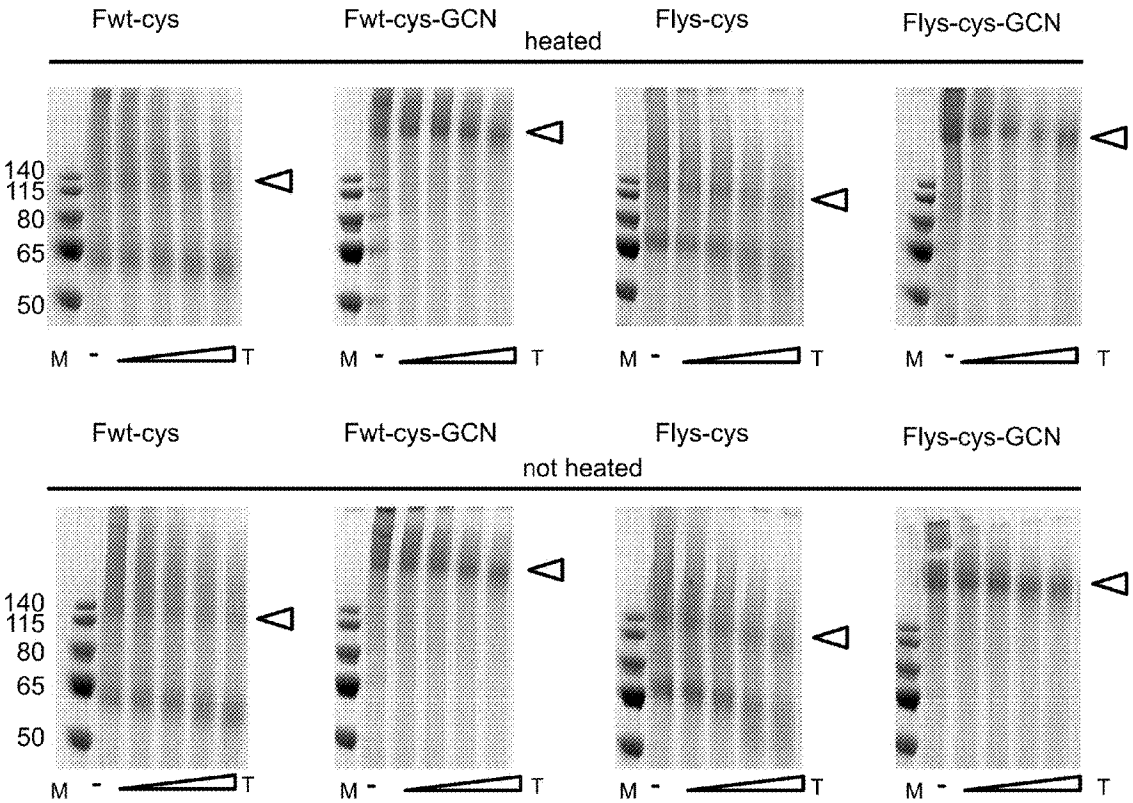
FIG. 9 shows a Coomassie Blue staining of gels on which Fwt-cys, Fwt-cys-GCN, Flys-cys and Flys-cys-GCN proteins were separated after heating (upper panels) or after no heating (lower panels) and increasing digestion with trypsin (T).
Figure 10A:
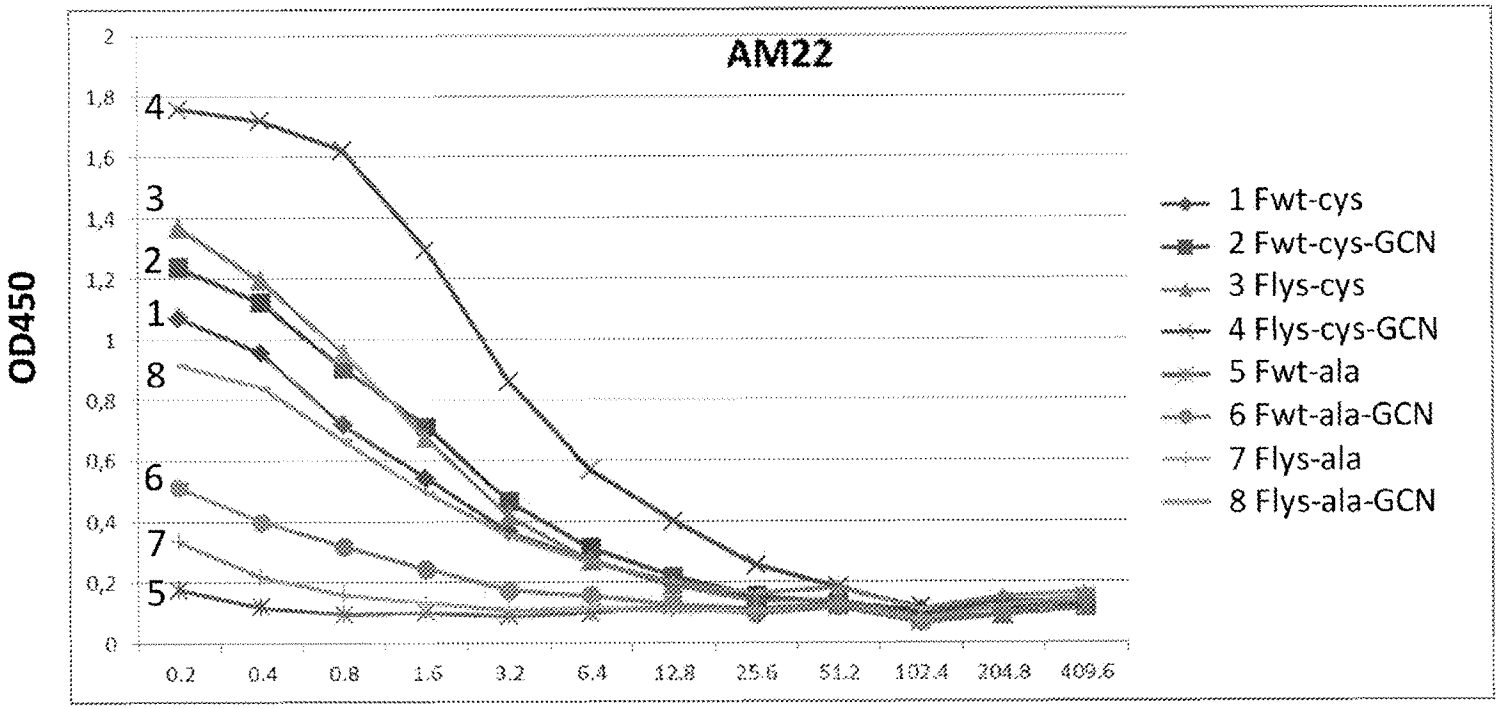
FIG. 10A shows the results of an ELISA assay with which the reactivity of different soluble F proteins with cysteine and alanine mutations in their HRB domain (Fwt-cys, Fwt-cys-GCN, Flys-cys, Flys-cys-GCN, Fwt-ala, Fwt-ala-GCN, Flys-ala, Flys-ala-GCN) with the AM22 conformational antibody was checked.
Figure 10B:
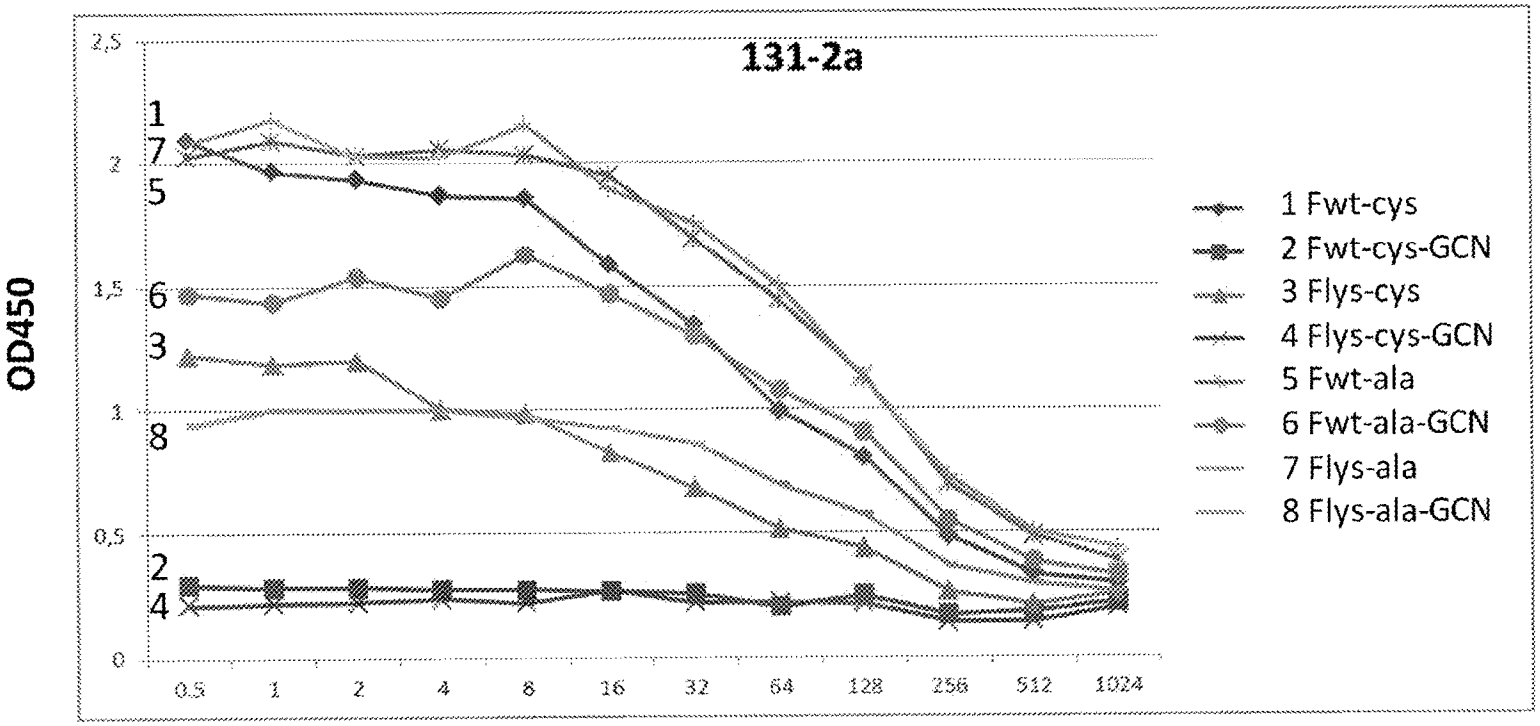
FIG. 10B shows the results of an ELISA assay with which the reactivity of different soluble F proteins with cysteine and alanine mutations in their HRB domain (Fwt-cys, Fwt-cys-GCN, Flys-cys, Flys-cys-GCN, Fwt-ala, Fwt-ala-GCN, Flys-ala, Flys-ala-GCN) with the 131-2a conformational antibody was checked.
Figure 10C:
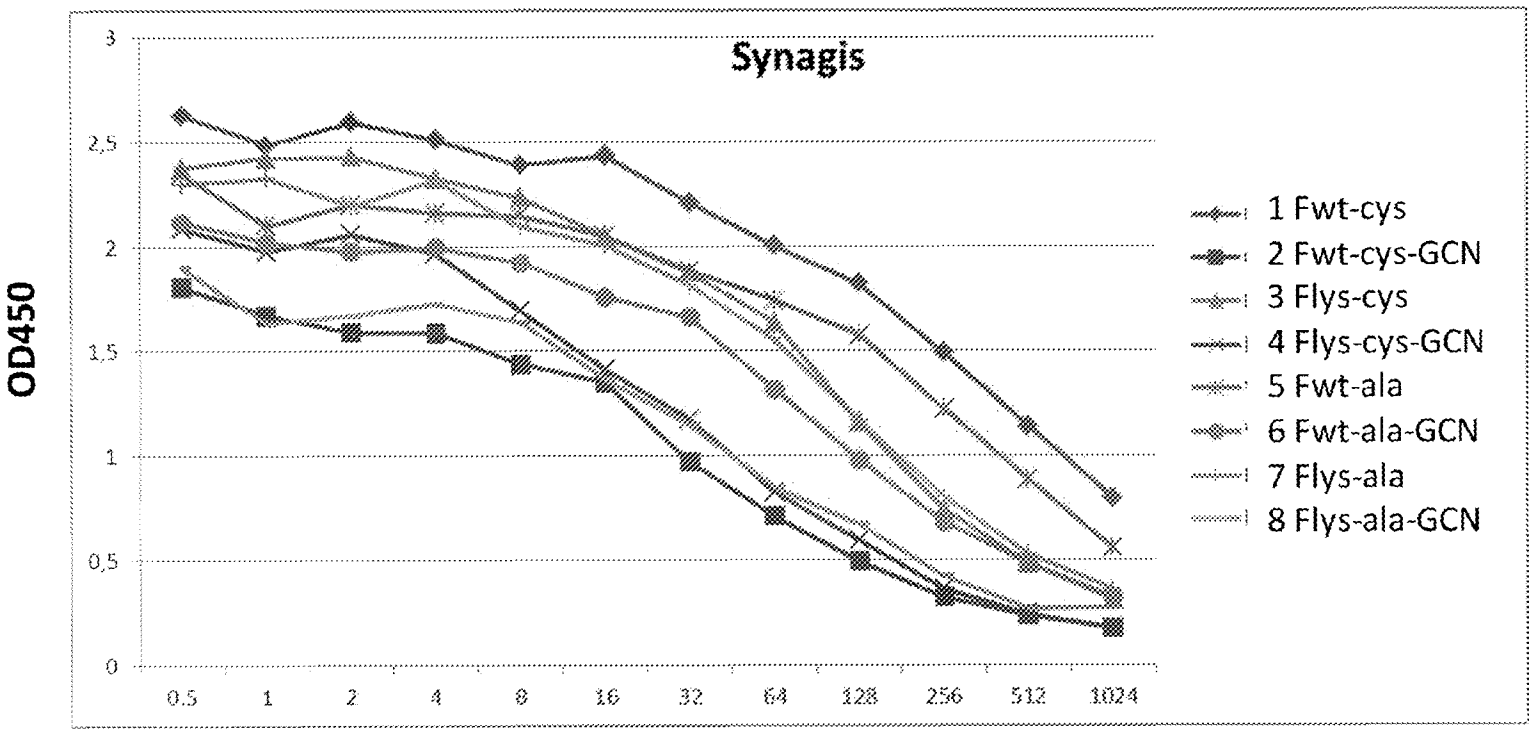
FIG. 10C shows the results of an ELISA assay with which the reactivity of different soluble F proteins with cysteine and alanine mutations in their HRB domain (Fwt-cys, Fwt-cys-GCN, Flys-cys, Flys-cys-GCN, Fwt-ala, Fwt-ala-GCN, Flys-ala, Flys-ala-GCN) with the Synagis® (Palivizumab) conformational antibody was checked.
Figure 10D:
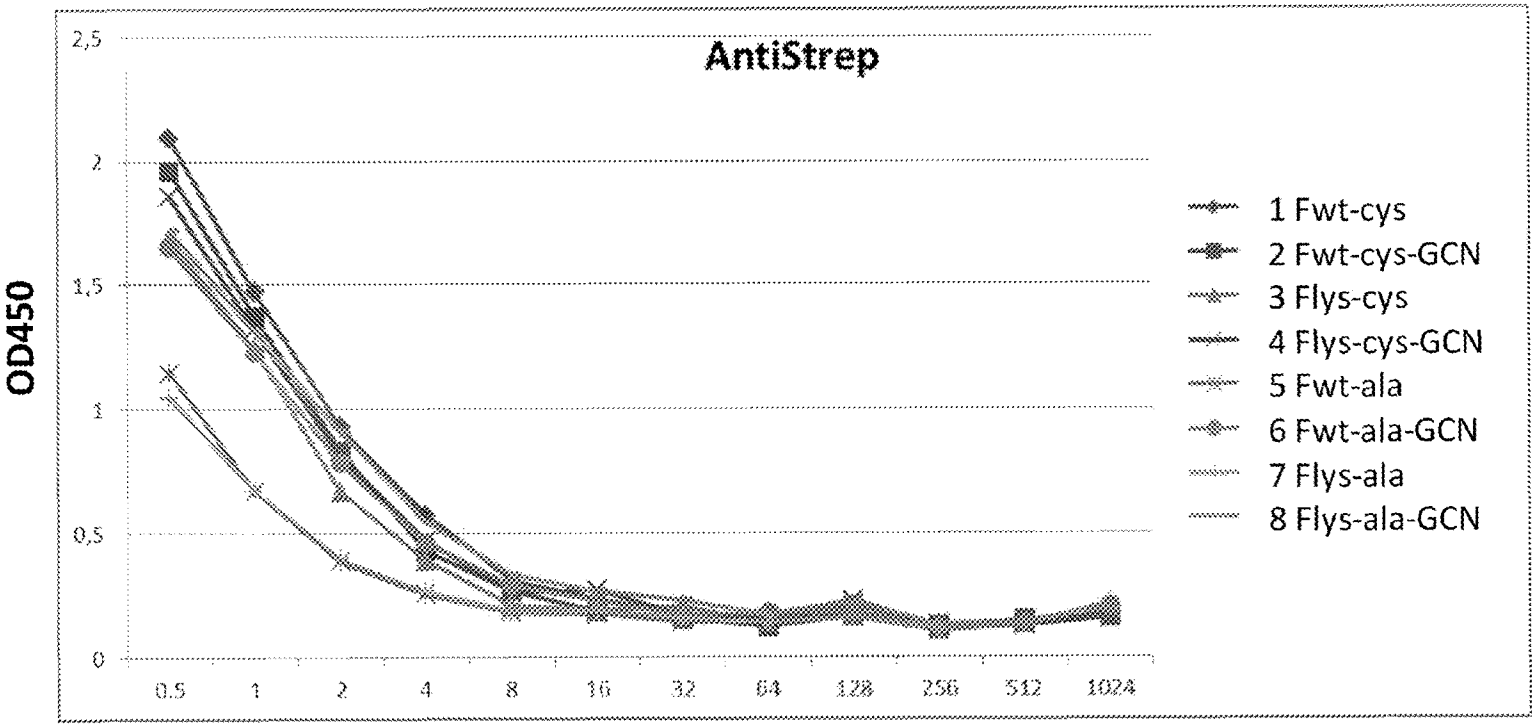
FIG. 10D shows the results of an ELISA assay with which the reactivity of different soluble F proteins with cysteine and alanine mutations in their HRB domain (Fwt-cys, Fwt-cys-GCN, Flys-cys, Flys-cys-GCN, Fwt-ala, Fwt-ala-GCN, Flys-ala, Flys-ala-GCN) with the anti-strep conformational antibody was checked.

To confirm and extend these observations, a subsequent experiment was performed in which the purified F proteins were subjected to limiting proteolysis followed by SDS-PAGE under non-reducing conditions. The results are shown in FIG. 9. The purified proteins were detected using Colloidal Coomassie Blue staining. Again, the higher order structures observed after introduction of the cysteine residues were shown not to be sensitive to heating of the sample prior to gel electrophoresis. Furthermore, the results indicate that trypsin-treated Fwt-cys and Flys-cys, which lack the GCN4 motif and are only present in a limited amount in the heat-resistant higher order structure, do not form higher structures when the samples were not heated prior to electrophoresis, as was observed for trypsin-treated Fwt and Flys (FIG. 6). From these results it was concluded that the higher structures observed after introduction of cysteine residues in HRB differ from the higher order structures that are observed for the cleaved F proteins with a wild type HRB, because, in contrast to the latter, the former are resistant to heating and are also formed when the F protein is not cleaved. Furthermore, the data show that introduction of cysteine residues in HRB prevents the formation of the heat-sensitive higher order structure. This indicates that these proteins do not assembly the 6HB that is present in the post-fusion conformation.

The reactivity of the cysteine mutant F proteins preparation was investigated with the RSV F specific MAbs Palivizumab, AM22 and 131-2a using the ELISA format (number 1-4 in FIG. 10), as outlined above. All cysteine mutant F proteins were coated with similar efficiencies as demonstrated by the binding of MAb specific for the Strep tag. Palivizumab displayed a concentration dependent binding to all F protein preparations, which differed only slightly between the different F preparations. MAbs 131-2a and AM22 displayed differential binding to the different F proteins. Fwt-cys-GCN and Flys-cys-GCN were not bound by 131-2a, but were clearly bound by AM22. These results indicate that the higher order structures that are observed for these two proteins correspond with stabilized pre-fusion F proteins (6HB−, 131-2a−, AM22+). The results also indicate that the epitope recognized by AM22 is affected to some extent by cleavage of F. Fwt-cys was efficiently recognized by 131-2a (Flys-cys somewhat less), in agreement that only part of these proteins form the pre-fusion higher order structure that is not reactive with this antibody. In agreement herewith, these preparations also reacted with AM22. The reactivity observed with AM22 may also be explained in part by Fwt-cys and Flys-cys being in some form of intermediate state (6HB−, 131-2a+, AM22+). While this may be expected for Flys-cys in view of the results with Flys, an alternative explanation must account for the intermediate phenotype of Fwt-cys. The introduction of the cysteines might also promote AM22 reactivity because of HRB not being able to bind HRA, as the inability to form the 6HB may be directly coupled to preservation of the AM22 epitope.

Example 3

Introduction of Alanine Residues in the HRB Region

Figure 11:
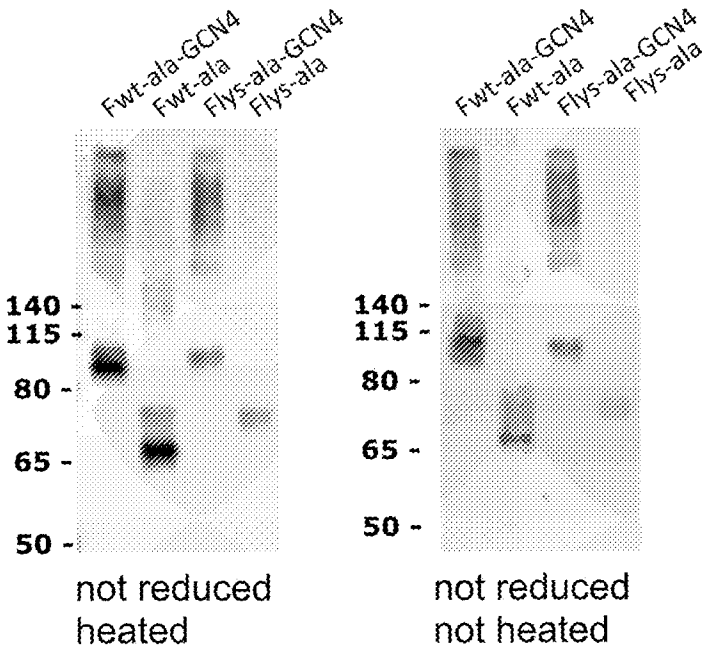
FIG. 11 displays western blots of Fwt-ala-GCN, Fwt-ala, Flys-ala-GCN and Flys-ala proteins that were either not reduced and heated (left panel) or both not reduced and not heated (right panel).

To study the effect of mutations in the HRB domain in more detail, mutant F proteins were produced in which the same amino acids as outlined in example 2 (see also Magro M et al. 2012. Proc Natl Acad Sci USA 109:3089-94) were substituted by alanines rather than cysteines (FIG. 4), to prevent the formation of a disulfide stabilized pre-fusion trimer. Also these proteins were subjected to SDS-PAGE analysis for the absence or presence of higher order structures. The results are shown in FIG. 11. Introduction of the alanine substitutions in the absence of GCN4 (construct referred to as Fwt-ala) prevented the formation of heat-sensitive higher order structures (6HB) under non-reducing conditions (compare FIG. 11 and FIG. 5), similarly as observed for Fwt-cys. In the presence of GCN4, some higher order structures were observed, which were not sensitive to heating of the sample prior to electrophoresis. These minor higher order structures may correspond with pre-fusion structures. Fwt-ala and Flys-ala, neither of which are able to assemble the 6HB, also do not react with AM22 (right top panel, line 5 and 6, FIG. 10), indicating that preventing the formation of the 6HB does not preserve the epitope for AM22. These proteins are probably in an intermediate state in which the stem formed by HRB in the prefusion proteins is dissociated, thereby making the epitope for 131-2a accessible. At the same time, the head domain is refolded resulting in loss of the epitope for AM22. Even so, the 6HB cannot be formed as a result of the alanine mutations in HRB, which probably prevent interaction of HRB with HRA. Introducing the GCN4 motif in these proteins (Fwt-ala-GCN and Flys-ala-GCN), probably results in a mixed population with some pre-fusion F proteins that are positive for AM22 but not 131-2a. As a result the reactivity of these proteins with AM22 increased, while their reactivity with 131-2a decreased. Strikingly, all F protein with alanine mutations in their HRB display decreased reactivity with AM22 when compared to their wild type HRB counterparts. Apparently, mutation of HRB may either help to preserve pre-fusion epitopes (F proteins with cysteine mutations in HRB) but may also decrease the reactivity with pre-fusion specific epitopes (F proteins with alanine mutations in HRB). Strikingly, these mutations are introduced at the same positions in the protein and both prevent 6HB formation to the same extent, indicating that the ability of the protein to adopt the post-fusion structure is not the driving force for the conformational change of the pre-fusion structure.

Figure 12A:
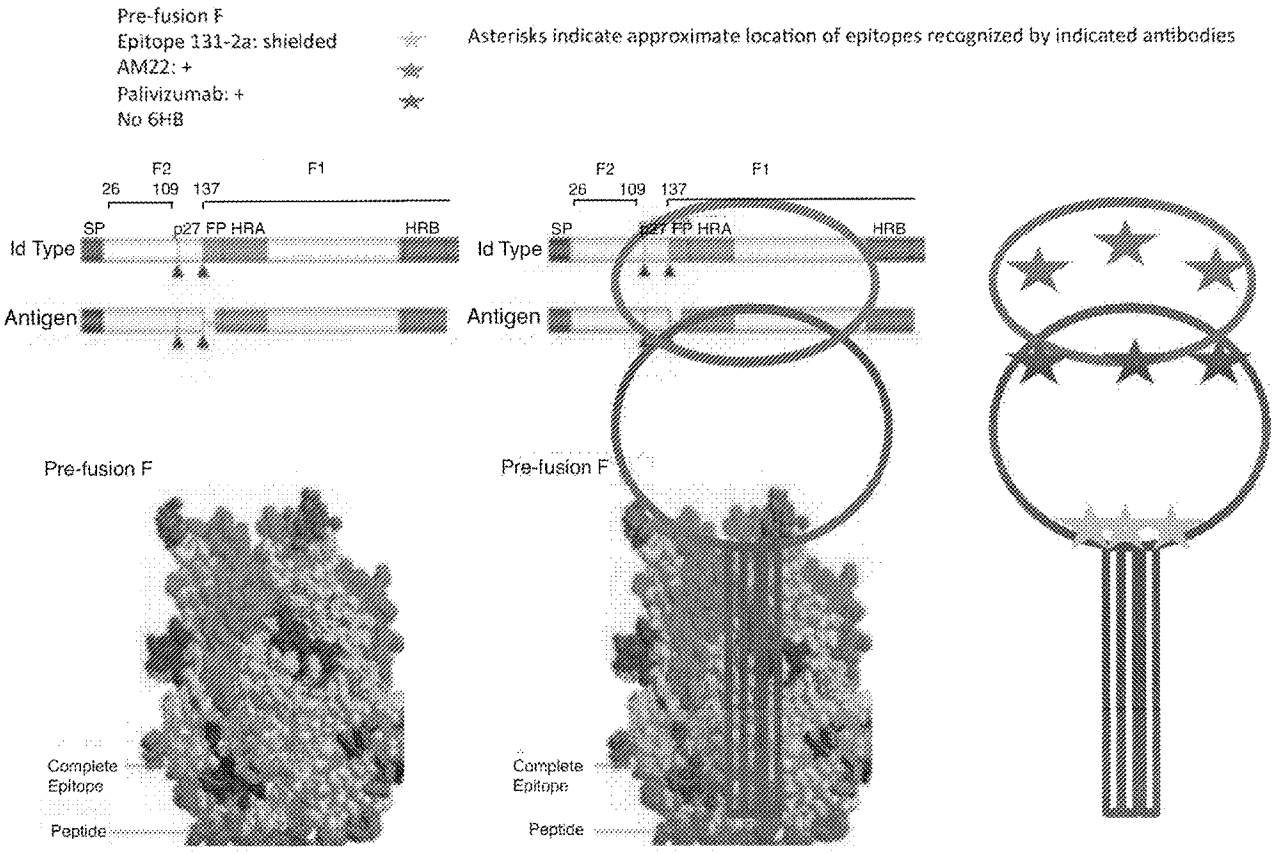
FIGS. 12A, B and C show the pre-fusion and post-fusion states of the F protein with the different epitopes of antibodies that are and are not available.
Figure 12B:
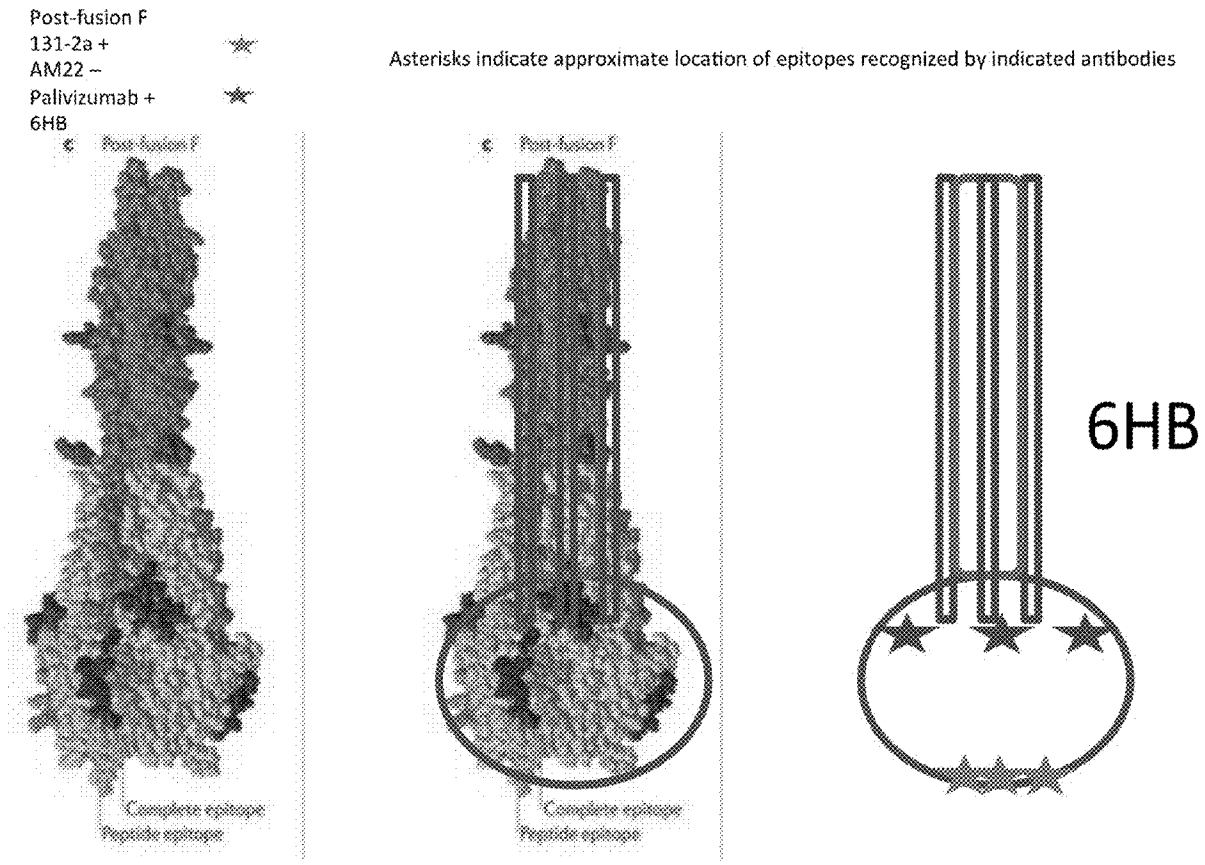
FIG. 12B shows that, in the post-fusion state of F protein where 6HB is present, the epitope for AM22 is shielded while the epitope for 131-2a is available.
Figure 12C:
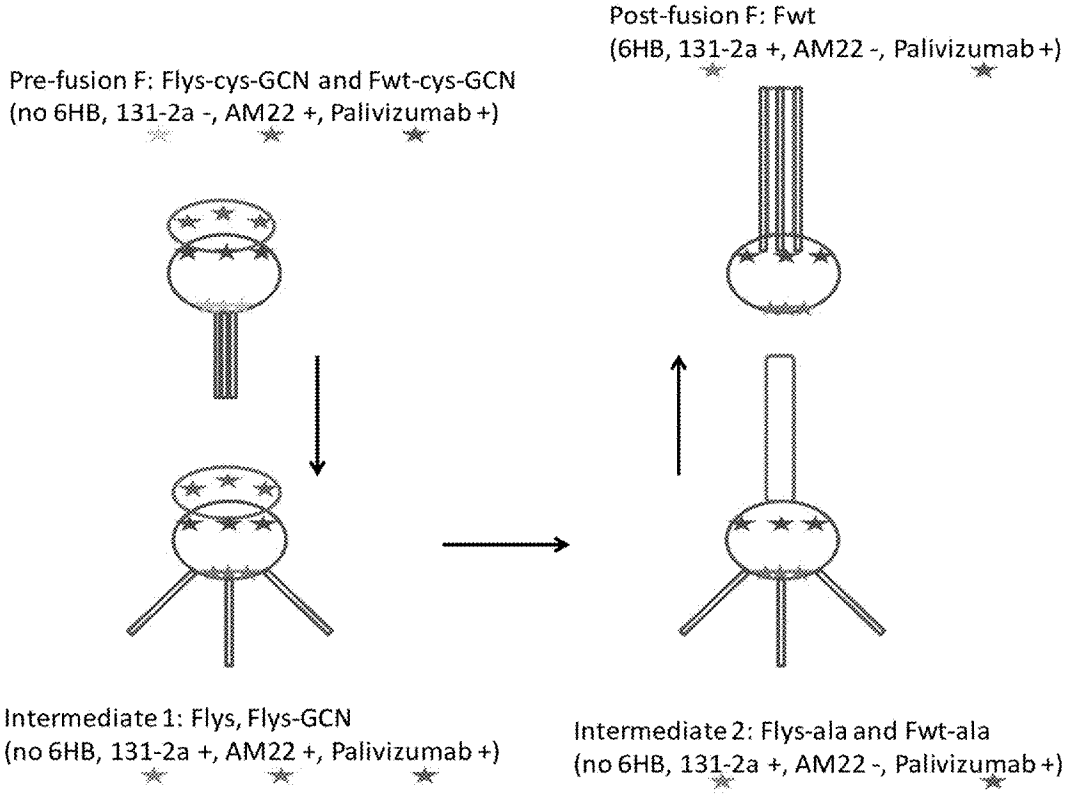
FIG. 12C shows the pre-fusion state of the F protein, absent the 6HB, transitioning through two intermediate states and ending in the post-fusion state exhibiting the 6HB, and also depicting the presence, appearance and disappearance of the various antigenic sites.

The disclosed data show that a set of assays was developed with which the conformation of recombinant soluble F proteins can be determined. With these assays four conformational states of the F protein can be discriminated that are schematically shown in FIGS. 12A and 12B:

1) Pre-fusion F (6HB−, 131-2a−, AM22+), see FIG. 12A left panel. Stable forms are Fwt-cys-GCN and Flys-cys-GCN;

2) Intermediate 1 (6HB−, 131-2a+, AM22+), see FIG. 12B left panel. The stem formed by HRB is dissociated, but the head domain with HRA is not yet refolded. Examples are Flys and Flys-GCN;

3) Intermediate 2 (6HB−, 131-2a+, AM22−), see FIG. 12B right panel. The stem formed by HRB is refolded, but also the head domain that probably contained the epitope recognized by AM22. The 6HB is however not yet assembled. Examples are Fwt-ala and Flys-ala;

4) Post-fusion F (6HB+, 131-2a+, AM22−), see FIG. 12A right panel. The best example is Fwt.

Example 4

Synthesis of Recombinant Soluble Proteins that Mimic the Pre-Fusion State of Human RSV F Protein In the examples above it is demonstrated that F proteins in the pre-fusion conformation are antigenically different from F proteins that have other conformations. The immune response specifically targeted against pre-fusion F epitopes, may be hampered by the presence of non-pre-fusion specific epitopes, the corresponding antibodies of which do not neutralize the virus (e.g. 131-2a). Although Fwt-cys-GCN and Flys-cys-GCN are in the pre-fusion conformation, these proteins are not considered suitable for the production of pre-fusion F proteins at a larger scale, primarily because these proteins are expressed at very low levels. To solve this, the inventors set out to device an alternative strategy to express high levels of recombinant F proteins that contain pre-fusion specific epitopes and lack post-fusion specific epitopes. The data show that GCN4 is able to confer the pre-fusion state onto recombinant proteins, but this only efficiently occurs when the HRB stem in the pre-fusion state is stabilized (e.g. in Fwt-cys-GCN and Flys-cys-GCN). This instability may even be increased by other mutations in HRB (such as the alanine mutations described herein).

The inventors hypothesized that there might be some form of inherent instability in HRB, which makes it possible for HRB to dissociate and subsequently to interact with the extended HRA. Rather than to try to stabilize HRB via the introduction of intermolecular disulfide bonds, which severely reduces protein expression levels, it was decided to remove the HRB region (and its inherent instability) altogether. However, in the complete absence of HRB it was expected that epitopes that are normally not available in the pre-fusion state would be exposed, either directly by removal of HRB (e.g. epitope of 131-2a) or because the resulting stem-less protein may behave as a monomer rather than a trimer. Furthermore, the data indicate that in the absence of cleavage the AM22 epitope and probably other pre-fusion specific epitopes are better maintained in the recombinant F protein (compare Flys-cys-GCN and Fwt-cys-GCN). In view of these considerations, a recombinant protein was generated, in which HRB was removed, the GCN4 trimerization motif was added and the furin cleavage site was mutated (FIG. 4). The HRB part of the ectodomain that was deleted is given in SEQ ID NO: 10. The full nucleotide sequence coding for the expressed polypeptide Flys-ΔHRB-GCN is provided in SEQ ID NO: 5, whereas the amino acid sequence is provided in SEQ ID NO: 6. As a control, a variant was synthesized that lacked GCN4 (SEQ ID NO: 3 and 4). The deletion in the constructs of the present invention is somewhat larger (namely position 478-512 in SEQ ID NO: 2) than is regarded as the HRB region in literature (Swanson et al. 2011, Proc Natl Acad Sci USA 10.1073. PNAS. 1106536108), which holds HRB to run from position 482-510 (in SEQ ID NO:2).

Figure 13:
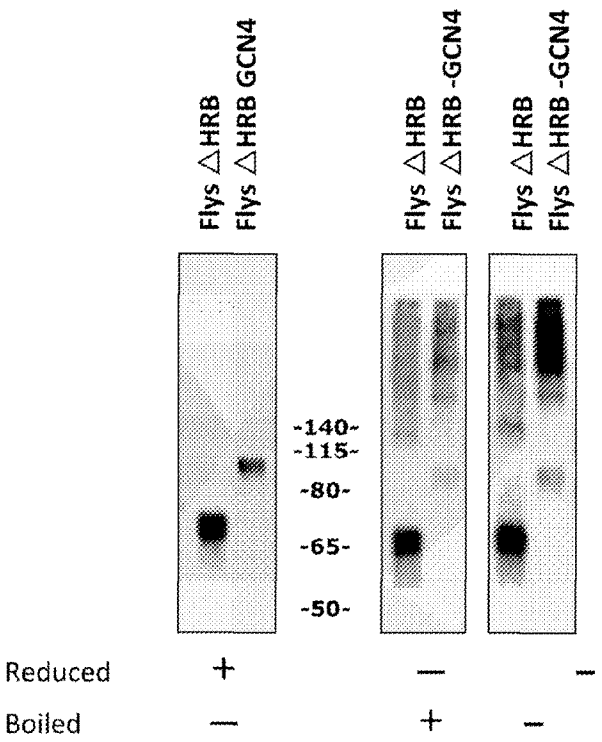
FIG. 13 shows the expression of Flys-ΔHRB and Flys-ΔHRB-GCN proteins on reducing (left panel) and non-reducing conditions (middle and right panel). The heat stability was checked as well (middle panel versus right panel).

These recombinant proteins were analyzed by SDS-PAGE using reducing and non-reducing conditions (FIG. 13). Both proteins migrated at the expected position in the reducing gel. However, in the absence of reducing agents the majority of Flys-ΔHRB-GCN ran at a much higher position in the gel. This was not the case for Flys-ΔHRB. Heating the samples did not affect the electrophoretic mobilities of the proteins much (FIG. 13, middle panel). This result indicates that the higher order structure observed for Flys-ΔHRB-GCN does not correspond to the heat-sensitive 6HB. This is expected because the 6HB cannot be formed in the absence of a functional HRB.

Figure 14:
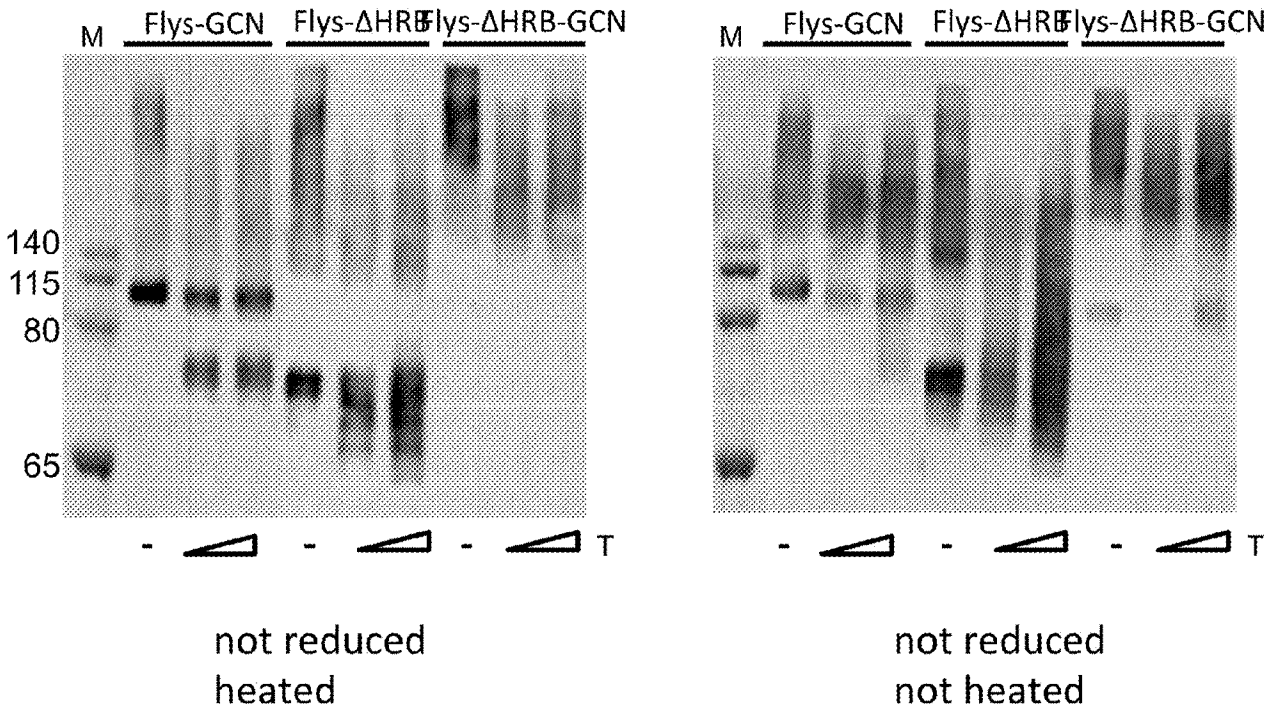
FIG. 14 shows a western blot with Flys-GCN, Flys-ΔHRB and Flys-ΔHRB-GCN under non-reducing conditions and after heat treatment (left panel) and no heat treatment (right panel). Increasing trypsin digestion is indicated (T). No trypsin treatment is indicated with a minus (–). Flys-ΔHRB-GCN forms higher order structures regardless of cleavage and regardless of heating of the purified product. These higher order structures do not relate to 6HB as a functional HRB domain is absent.
Figure 15A:
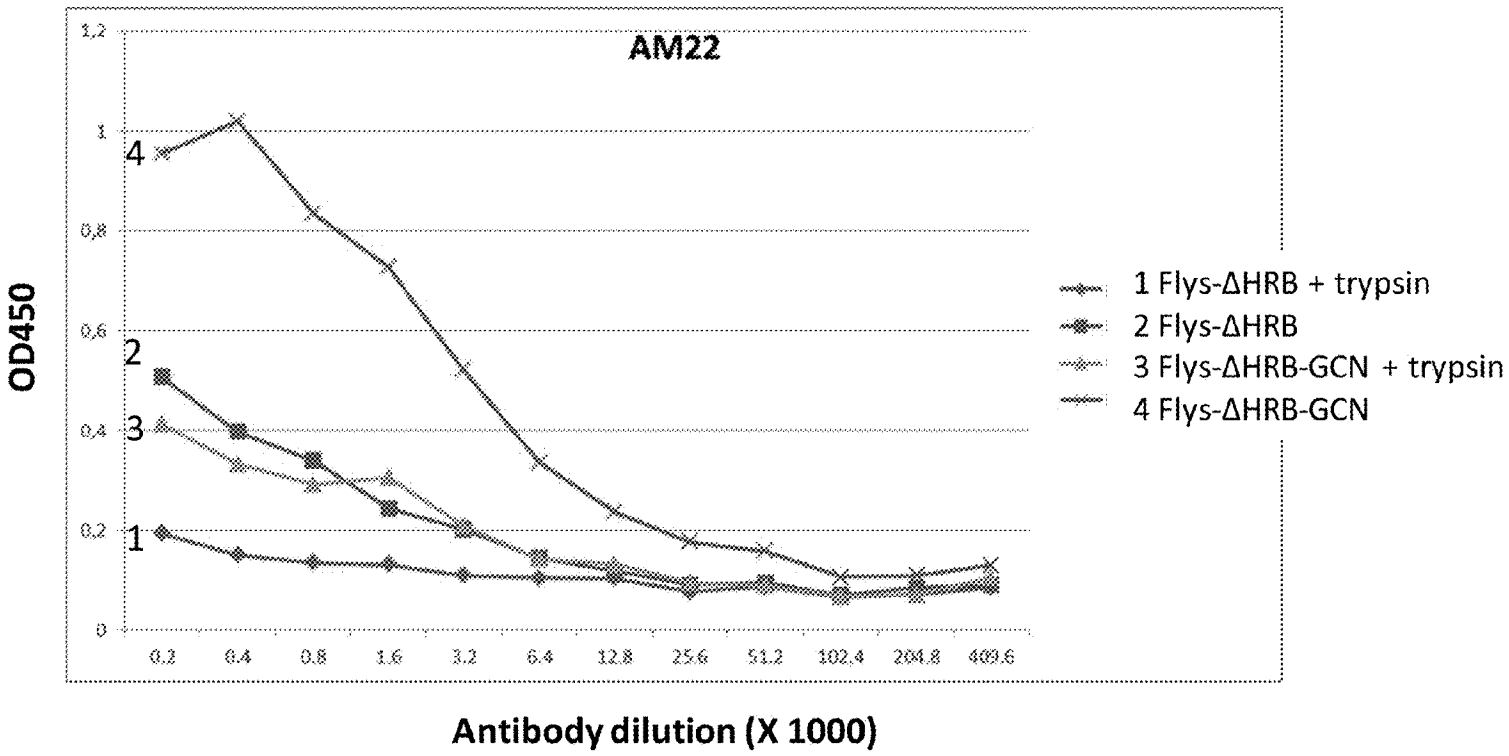
FIG. 15A shows the results of an ELISA assay with which the reactivity of two different soluble F proteins (Flys-ΔHRB and Flys-ΔHRB-GCN) with the AM22 conformational antibody was checked. The treatment with trypsin is indicated.
Figure 15B:
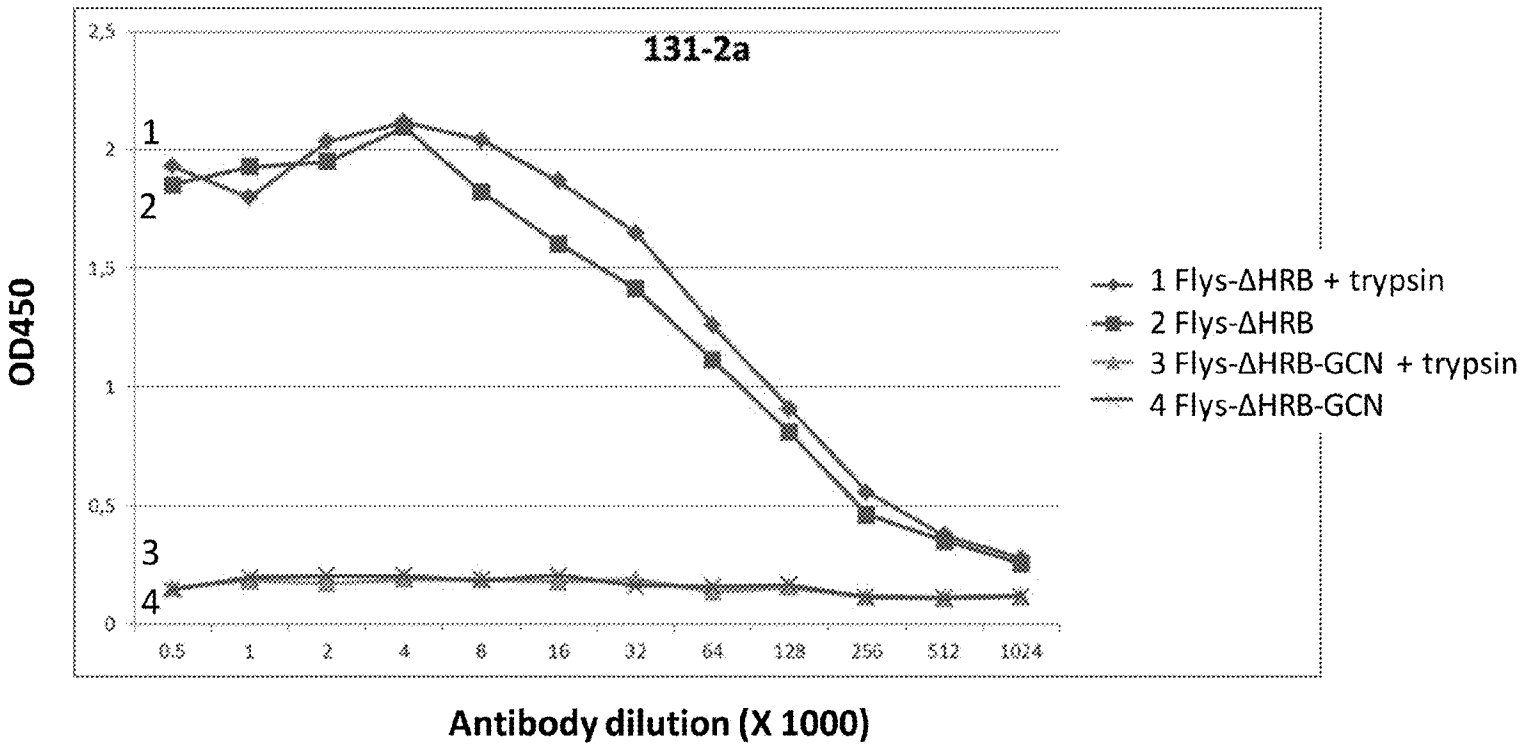
FIG. 15B shows the results of an ELISA assay with which the reactivity of two different soluble F proteins (Flys-ΔHRB and Flys-ΔHRB-GCN) with the 131-2a conformational antibody was checked. The treatment with trypsin is indicated.
Figure 15C:
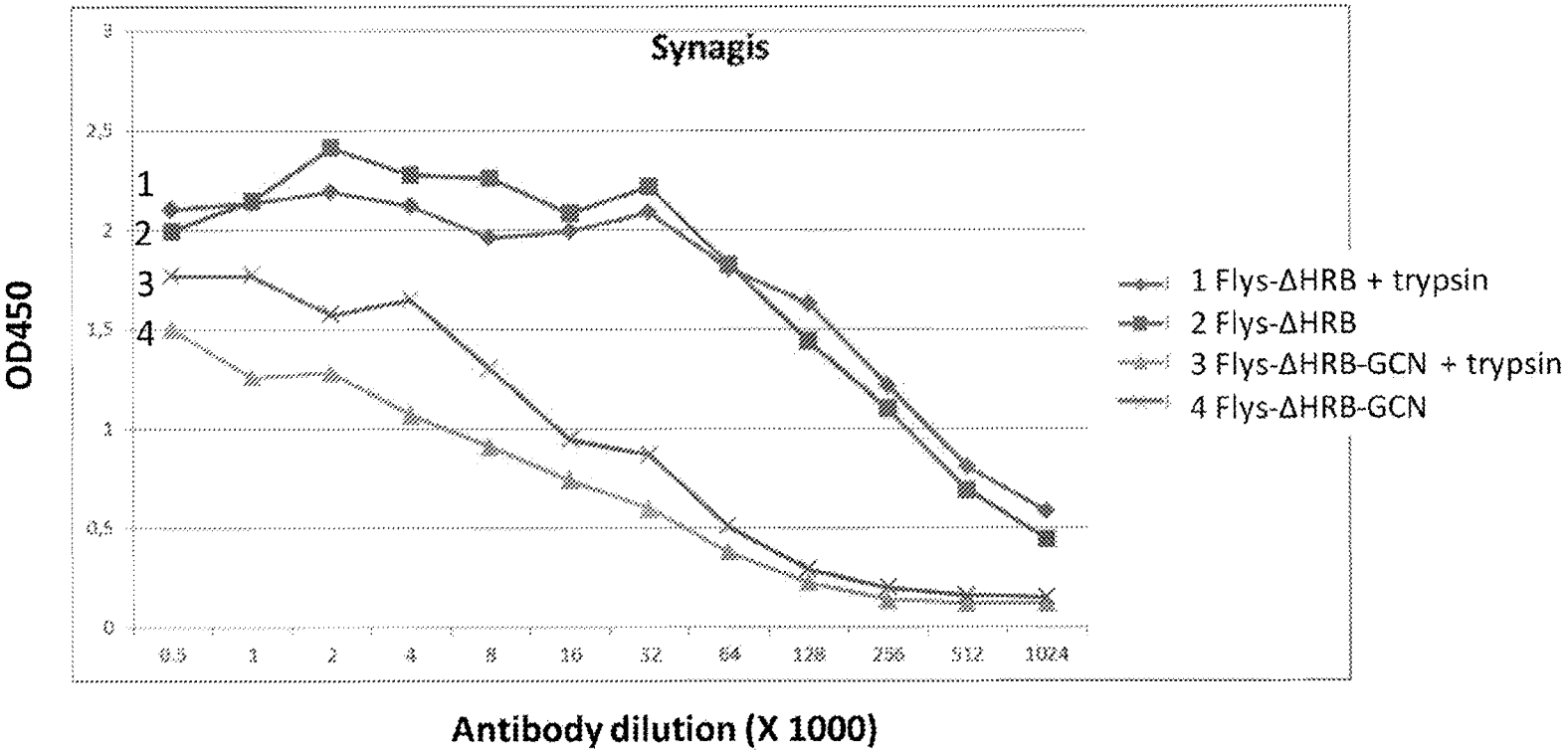
FIG. 15C shows the results of an ELISA assay with which the reactivity of two different soluble F proteins (Flys-ΔHRB and Flys-ΔHRB-GCN) with the Synagis® (Palivizumab) conformational antibody was checked. The treatment with trypsin is indicated.
Figure 15D:
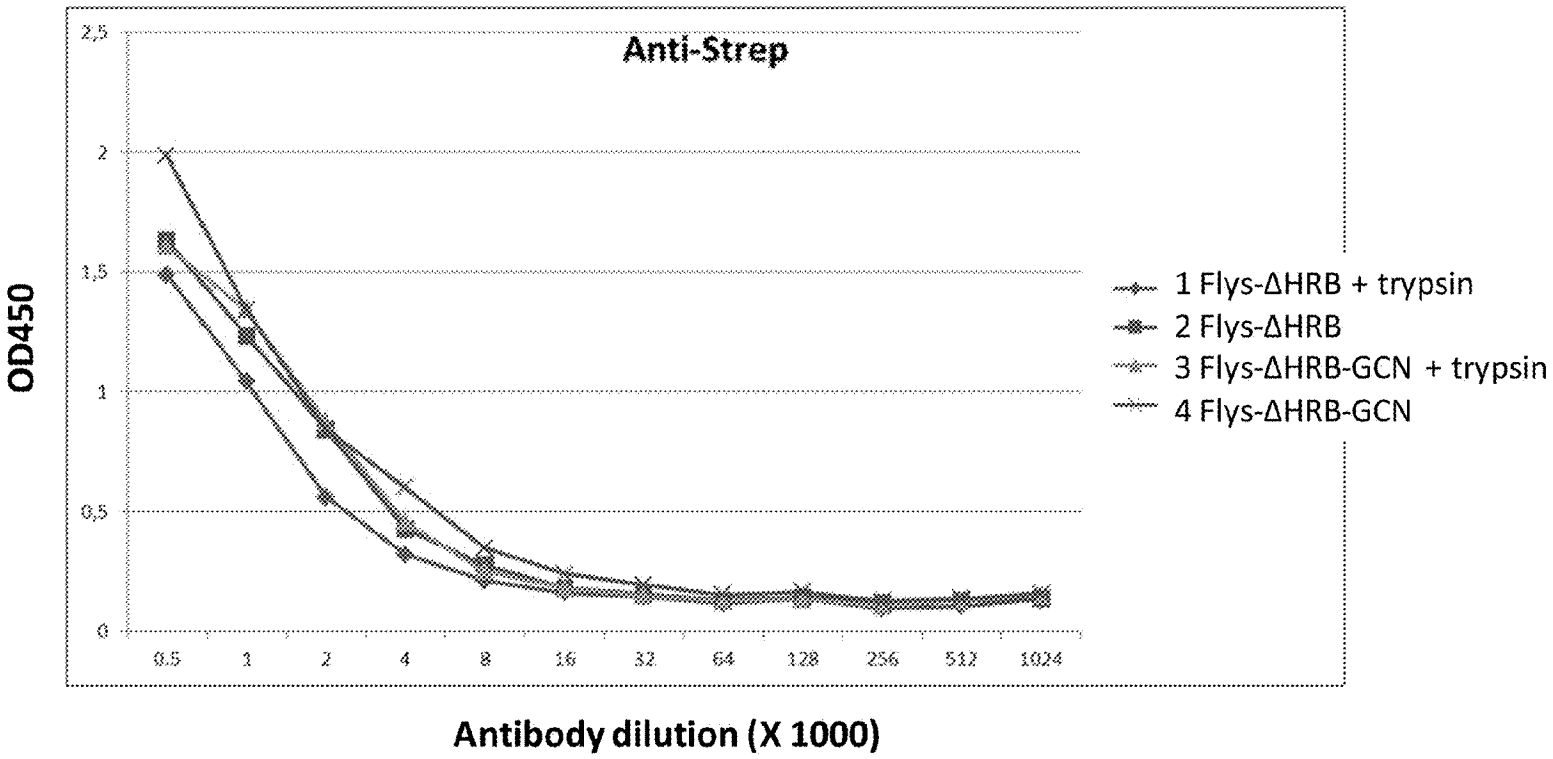
FIG. 15D shows the results of an ELISA assay with which the reactivity of two different soluble F proteins (Flys-ΔHRB and Flys-ΔHRB-GCN) with the anti-strep conformational antibody was checked. The treatment with trypsin is indicated.

Next, cleavage of these recombinant proteins was induced by trypsin treatment to study the effect of protein digestion on the protein conformation. As a control Flys-GCN was taken and proteins were run on non-reducing gels. The results are shown in FIG. 14. Upon trypsin treatment Flys-GCN, and in the absence of heating, the cleaved Flys-GCN protein ran as the (heat-sensitive) higher order structure indicative of 6HB formation. In contrast, the majority of Flys-ΔHRB ran at its expected (calculated) position in the gel, and trypsin cleavage did not induce the formation of higher order structures. This is expected as in the absence of HRB it is not possible to form the 6HB. The majority of Flys-ΔHRB-GCN4 again ran as a higher order structure, which was resistant to heat. This migration was not significantly affected by the trypsin treatment. The results show that replacing the HRB domain with GCN4 results in an extremely stable higher order structure that obviously does not correspond to the 6HB.

Figure 16:
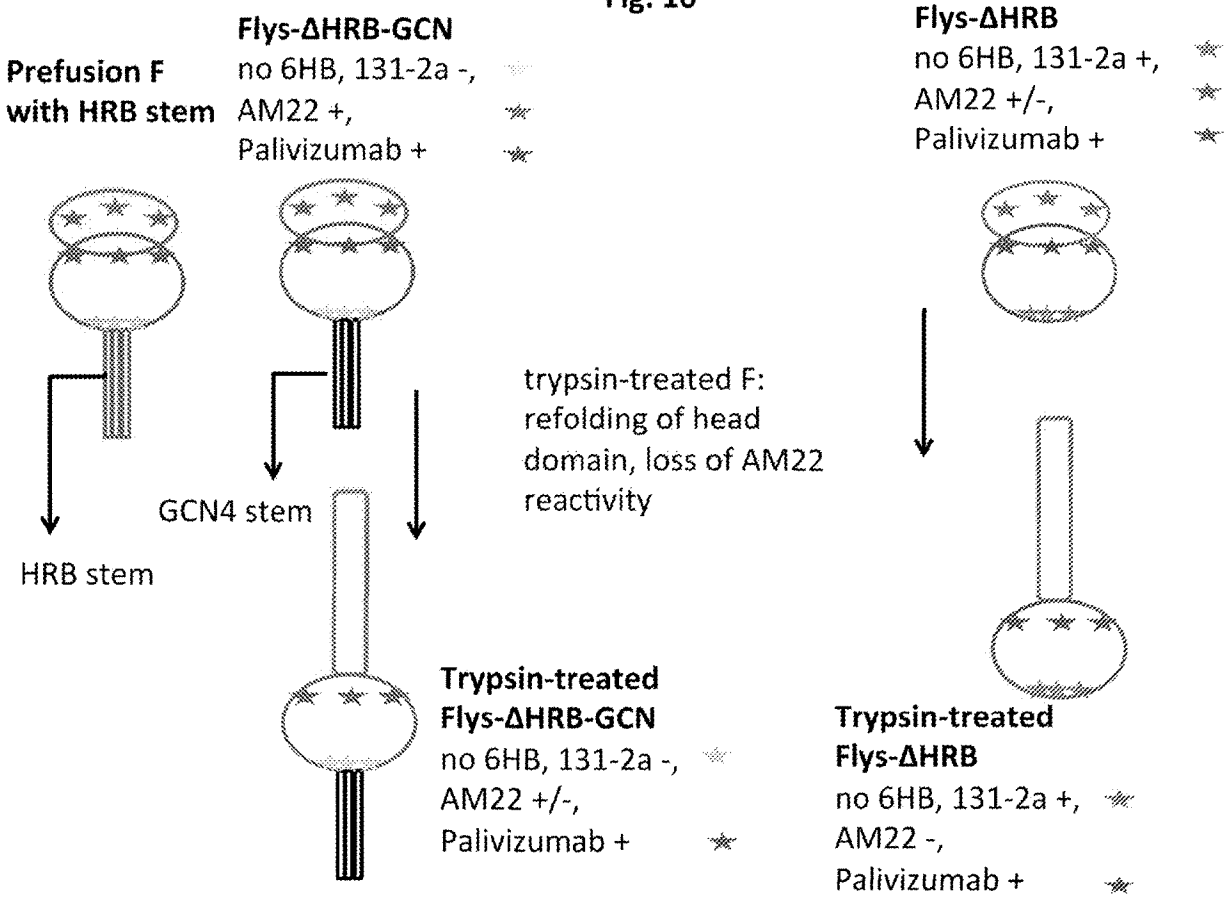
FIG. 16 is a schematic representation of the RSV F protein lacking a functional HRB domain.

The reactivity of the Flys-ΔHRB and Flys-ΔHRB-GCN proteins with the monoclonal antibodies was tested in an ELISA as outlined above (FIG. 15). Flys-ΔHRB was recognized both by 131-2a and AM22. In the additional presence of GCN4 (Flys-ΔHRB-GCN), the reactivity for 131-2a was lost, while the reactivity with AM22 increased. Apparently, the GCN4 domain shields the 131-2a epitope (similarly as a stabilized HRB) and stimulates the presence of the epitope of AM22. Trypsin treatment of the samples did not affect the 131-2a reactivity, but clearly decreased the AM22 reactivity. The reactivity with Palivizumab or the monoclonal against the strep tag was not affected by the trypsin treatment. From these results, it was concluded that Flys-ΔHRB-GCN is representative of the pre-fusion conformation of the RSV F protein as this protein does not form the 6HB, does react with AM22, but not with 131-2a (see for a schematic representation of this mutant, FIG. 16).

SEQUENCE LISTING

<160> NUMBER OF SEQ ID NOS: 20

<210> SEQ ID NO 1
<211> LENGTH: 1728
<212> TYPE: DNA
<213> ORGANISM: Respiratory Syncytial Virus

<400> SEQUENCE: 1 atggggtctc tgcaaccgct ggccaccttg tacctgctgg ggatgctggt cgcttccgtg 60 ctagcacaga atatcaccga ggagttttat cagagcacct gttcagccgt gagtaagggc 120 tacctgtcag cactgcggac tggatggtac accagtgtga tcactattga gctgtcaaac 180 atcaaggaaa acaaatgcaa tggcaccgac gctaaggtga aactgattaa gcaggagctg 240 gataagtaca aaaatgcagt gaccgaactg cagctgctga tgcagtcaac accagcagct 300 aacagccgag cacgaagaga gctgccccga ttcatgaact acacactgaa caacaccaag 360 aacacaaatg tgactctgag caagaaacgg aagaggcgct tcctggggtt tctgctggga 420 gtgggatcag caatcgccag cggcattgcc gtgagcaaag tcctgcacct ggagggggaa 480 gtgaacaaga tcaaatccgc tctgctgtct acaaacaagg cagtggtcag tctgtcaaat 540 ggcgtgagtg tcctgacttc aaaggtgctg gacctgaaaa attacatcga taagcagctg 600 ctgcctattg tcaacaaaca gagctgttcc atctctaata ttgagaccgt gatcgaattc 660 cagcagaaga acaatagact gctggagatt acaagggaat tttctgtgaa cgcaggcgtc 720 accacacccg tgagtacata catgctgact aatagcgagc tgctgtccct gatcaacgac 780 atgcctatta ccaatgatca gaagaaactg atgtccaaca atgtgcagat cgtcagacag 840 cagagttact caatcatgtc tatcattaag gaggaagtcc tggcttacgt ggtccagctg 900 ccactgtatg gagtgatcga cacaccctgc tggaaactgc atacttcacc tctgtgcact 960 accaacacaa aggaaggcag caatatttgc ctgacacgaa ctgaccgggg atggtactgt 1020 gataacgccg gcagcgtgtc cttctttcca caggctgaga cctgcaaggt ccagagcaac 1080 agggtgttct gtgacaccat gaattctctg acactgccta gtgaagtgaa cctgtgcaat 1140 atcgacatct tcaacccaaa gtacgattgt aagatcatga cctctaagac agatgtcagc 1200 tcctctgtga tcacttccct gggggcaatc gtgagctgct acggaaagac taaatgtacc 1260 gcctccaaca aaaatcgcgg gatcattaag accttcagca acggatgcga ctatgtctcc 1320 aacaagggcg tggatactgt gagtgtcggg aacaccctgt actatgtcaa taagcaggag 1380 ggaaaaagcc tgtacgtgaa gggcgaaccc atcattaact tttatgatcc cctggtcttc 1440 cctagcgacg agtttgatgc ctctatcagt caggtgaacg aaaaaatcaa tcagagcctg 1500 gcattcatcc gaaagagcga cgaactgctg cacaacttaa ttaatgacta caaggatgac 1560 gacgacaagg ctggacccgg ttggtcccat ccacagttcg agaagggcgg aggaagcgga 1620 ggcggctccg gaggaggatc ctggtcccac ccgcagtttg agaagggcgg cggcagcggc 1680 ggaggctccg gcggaggctc ctggagccac ccccagttcg agaagtaa 1728

<210> SEQ ID NO 2
<211> LENGTH: 575
<212> TYPE: PRT
<213> ORGANISM: Respiratory Syncytial Virus

<400> SEQUENCE: 2

Met Gly Ser Leu Gln Pro Leu Ala Thr Leu Tyr Leu Leu Gly Met Leu
1 5 10 15

```
Val Ala Ser Val Leu Ala Gln Asn Ile Thr Glu Glu Phe Tyr Gln Ser
            20                  25                  30

Thr Cys Ser Ala Val Ser Lys Gly Tyr Leu Ser Ala Leu Arg Thr Gly
        35                  40                  45

Trp Tyr Thr Ser Val Ile Thr Ile Glu Leu Ser Asn Ile Lys Glu Asn
    50                  55                  60

Lys Cys Asn Gly Thr Asp Ala Lys Val Lys Leu Ile Lys Gln Glu Leu
65                  70                  75                  80

Asp Lys Tyr Lys Asn Ala Val Thr Glu Leu Gln Leu Leu Met Gln Ser
                85                  90                  95

Thr Pro Ala Ala Asn Ser Arg Ala Arg Arg Glu Leu Pro Arg Phe Met
            100                 105                 110

Asn Tyr Thr Leu Asn Asn Thr Lys Asn Thr Asn Val Thr Leu Ser Lys
        115                 120                 125

Lys Arg Lys Arg Arg Phe Leu Gly Phe Leu Leu Gly Val Gly Ser Ala
    130                 135                 140

Ile Ala Ser Gly Ile Ala Val Ser Lys Val Leu His Leu Glu Gly Glu
145                 150                 155                 160

Val Asn Lys Ile Lys Ser Ala Leu Leu Ser Thr Asn Lys Ala Val Val
                165                 170                 175

Ser Leu Ser Asn Gly Val Ser Val Leu Thr Ser Lys Val Leu Asp Leu
            180                 185                 190

Lys Asn Tyr Ile Asp Lys Gln Leu Leu Pro Ile Val Asn Lys Gln Ser
        195                 200                 205

Cys Ser Ile Ser Asn Ile Glu Thr Val Ile Glu Phe Gln Gln Lys Asn
    210                 215                 220

Asn Arg Leu Leu Glu Ile Thr Arg Glu Phe Ser Val Asn Ala Gly Val
225                 230                 235                 240

Thr Thr Pro Val Ser Thr Tyr Met Leu Thr Asn Ser Glu Leu Leu Ser
                245                 250                 255

Leu Ile Asn Asp Met Pro Ile Thr Asn Asp Gln Lys Lys Leu Met Ser
            260                 265                 270

Asn Asn Val Gln Ile Val Arg Gln Gln Ser Tyr Ser Ile Met Ser Ile
        275                 280                 285

Ile Lys Glu Glu Val Leu Ala Tyr Val Val Gln Leu Pro Leu Tyr Gly
    290                 295                 300

Val Ile Asp Thr Pro Cys Trp Lys Leu His Thr Ser Pro Leu Cys Thr
305                 310                 315                 320

Thr Asn Thr Lys Glu Gly Ser Asn Ile Cys Leu Thr Arg Thr Asp Arg
                325                 330                 335

Gly Trp Tyr Cys Asp Asn Ala Gly Ser Val Ser Phe Phe Pro Gln Ala
            340                 345                 350

Glu Thr Cys Lys Val Gln Ser Asn Arg Val Phe Cys Asp Thr Met Asn
        355                 360                 365

Ser Leu Thr Leu Pro Ser Glu Val Asn Leu Cys Asn Ile Asp Ile Phe
    370                 375                 380

Asn Pro Lys Tyr Asp Cys Lys Ile Met Thr Ser Lys Thr Asp Val Ser
385                 390                 395                 400

Ser Ser Val Ile Thr Ser Leu Gly Ala Ile Val Ser Cys Tyr Gly Lys
                405                 410                 415

Thr Lys Cys Thr Ala Ser Asn Lys Asn Arg Gly Ile Ile Lys Thr Phe
            420                 425                 430

Ser Asn Gly Cys Asp Tyr Val Ser Asn Lys Gly Val Asp Thr Val Ser
```

```
        435                 440                 445

Val Gly Asn Thr Leu Tyr Tyr Val Asn Lys Gln Glu Gly Lys Ser Leu
    450                 455                 460

Tyr Val Lys Gly Glu Pro Ile Ile Asn Phe Tyr Asp Pro Leu Val Phe
465                 470                 475                 480

Pro Ser Asp Glu Phe Asp Ala Ser Ile Ser Gln Val Asn Glu Lys Ile
                485                 490                 495

Asn Gln Ser Leu Ala Phe Ile Arg Lys Ser Asp Glu Leu Leu His Asn
            500                 505                 510

Leu Ile Asn Asp Tyr Lys Asp Asp Asp Asp Lys Ala Gly Pro Gly Trp
        515                 520                 525

Ser His Pro Gln Phe Glu Lys Gly Gly Gly Ser Gly Gly Gly Ser Gly
    530                 535                 540

Gly Gly Ser Trp Ser His Pro Gln Phe Glu Lys Gly Gly Gly Ser Gly
545                 550                 555                 560

Gly Gly Ser Gly Gly Gly Ser Trp Ser His Pro Gln Phe Glu Lys
                565                 570                 575


<210> SEQ ID NO 3
<211> LENGTH: 1623
<212> TYPE: DNA
<213> ORGANISM: Respiratory Syncytial Virus

<400> SEQUENCE: 3

atggggtctc tgcaaccgct ggccaccttg tacctgctgg ggatgctggt cgcttccgtg     60

ctagcacaga atatcaccga ggagttttat cagtccacct gttccgcagt gtccaaaggc    120

tatctgtccg ccctgagaac cggctggtat acaagtgtga tcactattga gctgtcaaac    180

atcaaggaaa acaaatgcaa tggcaccgac gctaaggtga aactgattaa gcaggagctg    240

gataagtaca aaaatgcagt gaccgaactg cagctgctga tgcagtcaac accagccgct    300

aacagcaaag ccaagaaaga gctgccccgg ttcatgaatt atacactgaa caataccaag    360

aacacaaatg tgactctgag caagaaaaag aaaaagaaat tcctggggtt tctgctggga    420

gtgggatcag caatcgccag cggcattgcc gtgagcaaag tcctgcacct ggagggggaa    480

gtgaacaaga tcaaatccgc tctgctgtct acaaacaagg cagtggtcag tctgtcaaat    540

ggcgtgagtg tcctgacttc aaaggtgctg gacctgaaaa attacatcga taagcagctg    600

ctgcctattg tcaacaaaca gagctgttcc atctctaata ttgagaccgt gatcgaattc    660

cagcagaaga acaataggct gctggagatt acacgcgaat tttctgtgaa cgcaggcgtc    720

accacacccg tgagtacata catgctgact aatagcgagc tgctgtccct gatcaacgac    780

atgcctatta ccaatgatca gaagaaactg atgtccaaca atgtgcagat cgtccggcag    840

cagagttact caatcatgtc tatcattaag gaggaagtcc tggcttacgt ggtccagctg    900

ccactgtatg gagtgatcga cacaccctgc tggaaactgc atactagccc cctgtgcact    960

accaacacaa aggaaggcag caatatttgc ctgacacgga ctgacagagg atggtactgt   1020

gataacgccg gcagcgtgtc cttctttcca caggctgaga cctgcaaggt ccagagcaac   1080

cgagtgttct gtgacaccat gaattctctg acactgccta gtgaagtgaa cctgtgcaat   1140

atcgacatct tcaacccaaa gtacgattgt aagatcatga cctctaagac agatgtcagc   1200

tcctctgtga tcacttccct gggggcaatc gtgagctgct acggaaagac taaatgtacc   1260

gcctccaaca aaaatagagg gatcattaag accttcagca acggatgcga ctatgtctcc   1320

aacaagggcg tggatactgt gagtgtcggg aacaccctgt actatgtcaa taagcaggag   1380
```

```
ggaaaaagcc tgtacgtgaa gggcgaaccc atcattaact tttatgatcc cttaattaat   1440

gactacaagg atgacgacga caaggctgga cccggttggt cccatccaca gttcgagaag   1500

ggcggaggaa gcggaggcgg ctccggagga ggatcctggt cccacccgca gtttgagaag   1560

ggcggcggca gcggcggagg ctccggcgga ggctcctgga gccacccccca gttcgagaag   1620

taa                                                                 1623


<210> SEQ ID NO 4
<211> LENGTH: 540
<212> TYPE: PRT
<213> ORGANISM: Respiratory Syncytial Virus

<400> SEQUENCE: 4

Met Gly Ser Leu Gln Pro Leu Ala Thr Leu Tyr Leu Leu Gly Met Leu
1               5                   10                  15

Val Ala Ser Val Leu Ala Gln Asn Ile Thr Glu Glu Phe Tyr Gln Ser
            20                  25                  30

Thr Cys Ser Ala Val Ser Lys Gly Tyr Leu Ser Ala Leu Arg Thr Gly
        35                  40                  45

Trp Tyr Thr Ser Val Ile Thr Ile Glu Leu Ser Asn Ile Lys Glu Asn
    50                  55                  60

Lys Cys Asn Gly Thr Asp Ala Lys Val Lys Leu Ile Lys Gln Glu Leu
65                  70                  75                  80

Asp Lys Tyr Lys Asn Ala Val Thr Glu Leu Gln Leu Leu Met Gln Ser
                85                  90                  95

Thr Pro Ala Ala Asn Ser Lys Ala Lys Lys Glu Leu Pro Arg Phe Met
            100                 105                 110

Asn Tyr Thr Leu Asn Asn Thr Lys Asn Thr Asn Val Thr Leu Ser Lys
        115                 120                 125

Lys Lys Lys Lys Lys Phe Leu Gly Phe Leu Leu Gly Val Gly Ser Ala
    130                 135                 140

Ile Ala Ser Gly Ile Ala Val Ser Lys Val Leu His Leu Glu Gly Glu
145                 150                 155                 160

Val Asn Lys Ile Lys Ser Ala Leu Leu Ser Thr Asn Lys Ala Val Val
                165                 170                 175

Ser Leu Ser Asn Gly Val Ser Val Leu Thr Ser Lys Val Leu Asp Leu
            180                 185                 190

Lys Asn Tyr Ile Asp Lys Gln Leu Leu Pro Ile Val Asn Lys Gln Ser
        195                 200                 205

Cys Ser Ile Ser Asn Ile Glu Thr Val Ile Glu Phe Gln Gln Lys Asn
    210                 215                 220

Asn Arg Leu Leu Glu Ile Thr Arg Glu Phe Ser Val Asn Ala Gly Val
225                 230                 235                 240

Thr Thr Pro Val Ser Thr Tyr Met Leu Thr Asn Ser Glu Leu Leu Ser
                245                 250                 255

Leu Ile Asn Asp Met Pro Ile Thr Asn Asp Gln Lys Lys Leu Met Ser
            260                 265                 270

Asn Asn Val Gln Ile Val Arg Gln Gln Ser Tyr Ser Ile Met Ser Ile
        275                 280                 285

Ile Lys Glu Glu Val Leu Ala Tyr Val Val Gln Leu Pro Leu Tyr Gly
    290                 295                 300

Val Ile Asp Thr Pro Cys Trp Lys Leu His Thr Ser Pro Leu Cys Thr
305                 310                 315                 320
```

```
Thr Asn Thr Lys Glu Gly Ser Asn Ile Cys Leu Thr Arg Thr Asp Arg
                325                 330                 335

Gly Trp Tyr Cys Asp Asn Ala Gly Ser Val Ser Phe Phe Pro Gln Ala
            340                 345                 350

Glu Thr Cys Lys Val Gln Ser Asn Arg Val Phe Cys Asp Thr Met Asn
        355                 360                 365

Ser Leu Thr Leu Pro Ser Glu Val Asn Leu Cys Asn Ile Asp Ile Phe
    370                 375                 380

Asn Pro Lys Tyr Asp Cys Lys Ile Met Thr Ser Lys Thr Asp Val Ser
385                 390                 395                 400

Ser Ser Val Ile Thr Ser Leu Gly Ala Ile Val Ser Cys Tyr Gly Lys
                405                 410                 415

Thr Lys Cys Thr Ala Ser Asn Lys Asn Arg Gly Ile Ile Lys Thr Phe
            420                 425                 430

Ser Asn Gly Cys Asp Tyr Val Ser Asn Lys Gly Val Asp Thr Val Ser
        435                 440                 445

Val Gly Asn Thr Leu Tyr Tyr Val Asn Lys Gln Glu Gly Lys Ser Leu
    450                 455                 460

Tyr Val Lys Gly Glu Pro Ile Ile Asn Phe Tyr Asp Pro Leu Ile Asn
465                 470                 475                 480

Asp Tyr Lys Asp Asp Asp Asp Lys Ala Gly Pro Gly Trp Ser His Pro
                485                 490                 495

Gln Phe Glu Lys Gly Gly Gly Ser Gly Gly Gly Ser Gly Gly Gly Ser
            500                 505                 510

Trp Ser His Pro Gln Phe Glu Lys Gly Gly Gly Ser Gly Gly Gly Ser
        515                 520                 525

Gly Gly Gly Ser Trp Ser His Pro Gln Phe Glu Lys
    530                 535                 540


<210> SEQ ID NO 5
<211> LENGTH: 2010
<212> TYPE: DNA
<213> ORGANISM: Respiratory Syncytial Virus

<400> SEQUENCE: 5

atggggtctc tgcaaccgct ggccaccttg tacctgctgg ggatgctggt cgcttccgtg     60

ctagcacaga atatcaccga ggagttttat cagtccacct gttccgcagt gtccaaaggc    120

tatctgtccg ccctgagaac cggctggtat acaagtgtga tcactattga gctgtcaaac    180

atcaaggaaa acaaatgcaa tggcaccgac gctaaggtga aactgattaa gcaggagctg    240

gataagtaca aaaatgcagt gaccgaactg cagctgctga tgcagtcaac accagccgct    300

aacagcaaag ccaagaaaga gctgccccgg ttcatgaatt atacactgaa caataccaag    360

aacacaaatg tgactctgag caagaaaaag aaaaagaaat tcctggggtt tctgctggga    420

gtgggatcag caatcgccag cggcattgcc gtgagcaaag tcctgcacct ggagggggaa    480

gtgaacaaga tcaaatccgc tctgctgtct acaaacaagg cagtggtcag tctgtcaaat    540

ggcgtgagtg tcctgacttc aaaggtgctg gacctgaaaa attacatcga taagcagctg    600

ctgcctattg tcaacaaaca gagctgttcc atctctaata ttgagaccgt gatcgaattc    660

cagcagaaga acaataggct gctggagatt acacgcgaat tttctgtgaa cgcaggcgtc    720

accacacccg tgagtacata catgctgact aatagcgagc tgctgtccct gatcaacgac    780

atgcctatta ccaatgatca gaagaaactg atgtccaaca atgtgcagat cgtccggcag    840

cagagttact caatcatgtc tatcattaag gaggaagtcc tggcttacgt ggtccagctg    900
```

```
ccactgtatg gagtgatcga cacaccctgc tggaaactgc atactagccc cctgtgcact    960

accaacacaa aggaaggcag caatatttgc ctgacacgga ctgacagagg atggtactgt   1020

gataacgccg gcagcgtgtc cttctttcca caggctgaga cctgcaaggt ccagagcaac   1080

cgagtgttct gtgacaccat gaattctctg acactgccta gtgaagtgaa cctgtgcaat   1140

atcgacatct tcaacccaaa gtacgattgt aagatcatga cctctaagac agatgtcagc   1200

tcctctgtga tcacttccct gggggcaatc gtgagctgct acggaaagac taaatgtacc   1260

gcctccaaca aaaatagagg gatcattaag accttcagca acggatgcga ctatgtctcc   1320

aacaagggcg tggatactgt gagtgtcggg aacaccctgt actatgtcaa taagcaggag   1380

ggaaaaagcc tgtacgtgaa gggcgaaccc atcattaact tttatgatcc cttaattaag   1440

aggatgaaac agattgagga taaaatcgag gaaattgaaa gcaagcagaa gaaaattgag   1500

aacgaaatcg cccgcattaa gaaagggaat accaactccg gcgggtctac aactaccatc   1560

acaaacaata acagtggaac taacagttca agcacaactt acaccgtgaa gtctggcgat   1620

acactgtggg ggatctcaca gcgatatggc atcagcgtgg ctcagattca gtccgcaaat   1680

aacctgaaat ctaccatcat ctacatcggg cagaagctgg tgctgactgg aagcgcctcc   1740

tctaccaaca gtggaggctc aaataactca gcttccacca caccaactac cagcgtgacc   1800

cccgcaaagc ctacatcaca gactaccgac tacaaggatg acgacgacaa ggctggaccc   1860

ggttggtccc atccacagtt cgagaagggc ggaggaagcg gaggcggctc cggaggagga   1920

tcctggtccc acccgcagtt tgagaagggc ggcggcagcg gcggaggctc cggcggaggc   1980

tcctggagcc acccccagtt cgagaagtaa                                    2010
```

<210> SEQ ID NO 6
<211> LENGTH: 669
<212> TYPE: PRT
<213> ORGANISM: Respiratory Syncytial Virus

<400> SEQUENCE: 6

```
Met Gly Ser Leu Gln Pro Leu Ala Thr Leu Tyr Leu Leu Gly Met Leu
1               5                   10                  15

Val Ala Ser Val Leu Ala Gln Asn Ile Thr Glu Glu Phe Tyr Gln Ser
            20                  25                  30

Thr Cys Ser Ala Val Ser Lys Gly Tyr Leu Ser Ala Leu Arg Thr Gly
        35                  40                  45

Trp Tyr Thr Ser Val Ile Thr Ile Glu Leu Ser Asn Ile Lys Glu Asn
    50                  55                  60

Lys Cys Asn Gly Thr Asp Ala Lys Val Lys Leu Ile Lys Gln Glu Leu
65                  70                  75                  80

Asp Lys Tyr Lys Asn Ala Val Thr Glu Leu Gln Leu Leu Met Gln Ser
                85                  90                  95

Thr Pro Ala Ala Asn Ser Lys Ala Lys Lys Glu Leu Pro Arg Phe Met
            100                 105                 110

Asn Tyr Thr Leu Asn Asn Thr Lys Asn Thr Asn Val Thr Leu Ser Lys
        115                 120                 125

Lys Lys Lys Lys Lys Phe Leu Gly Phe Leu Leu Gly Val Gly Ser Ala
    130                 135                 140

Ile Ala Ser Gly Ile Ala Val Ser Lys Val Leu His Leu Glu Gly Glu
145                 150                 155                 160

Val Asn Lys Ile Lys Ser Ala Leu Leu Ser Thr Asn Lys Ala Val Val
                165                 170                 175
```

```
Ser Leu Ser Asn Gly Val Ser Val Leu Thr Ser Lys Val Leu Asp Leu
            180                 185                 190

Lys Asn Tyr Ile Asp Lys Gln Leu Leu Pro Ile Val Asn Lys Gln Ser
        195                 200                 205

Cys Ser Ile Ser Asn Ile Glu Thr Val Ile Glu Phe Gln Gln Lys Asn
    210                 215                 220

Asn Arg Leu Leu Glu Ile Thr Arg Glu Phe Ser Val Asn Ala Gly Val
225                 230                 235                 240

Thr Thr Pro Val Ser Thr Tyr Met Leu Thr Asn Ser Glu Leu Leu Ser
                245                 250                 255

Leu Ile Asn Asp Met Pro Ile Thr Asn Asp Gln Lys Lys Leu Met Ser
            260                 265                 270

Asn Asn Val Gln Ile Val Arg Gln Gln Ser Tyr Ser Ile Met Ser Ile
        275                 280                 285

Ile Lys Glu Glu Val Leu Ala Tyr Val Val Gln Leu Pro Leu Tyr Gly
    290                 295                 300

Val Ile Asp Thr Pro Cys Trp Lys Leu His Thr Ser Pro Leu Cys Thr
305                 310                 315                 320

Thr Asn Thr Lys Glu Gly Ser Asn Ile Cys Leu Thr Arg Thr Asp Arg
                325                 330                 335

Gly Trp Tyr Cys Asp Asn Ala Gly Ser Val Ser Phe Phe Pro Gln Ala
            340                 345                 350

Glu Thr Cys Lys Val Gln Ser Asn Arg Val Phe Cys Asp Thr Met Asn
        355                 360                 365

Ser Leu Thr Leu Pro Ser Glu Val Asn Leu Cys Asn Ile Asp Ile Phe
    370                 375                 380

Asn Pro Lys Tyr Asp Cys Lys Ile Met Thr Ser Lys Thr Asp Val Ser
385                 390                 395                 400

Ser Ser Val Ile Thr Ser Leu Gly Ala Ile Val Ser Cys Tyr Gly Lys
                405                 410                 415

Thr Lys Cys Thr Ala Ser Asn Lys Asn Arg Gly Ile Ile Lys Thr Phe
            420                 425                 430

Ser Asn Gly Cys Asp Tyr Val Ser Asn Lys Gly Val Asp Thr Val Ser
        435                 440                 445

Val Gly Asn Thr Leu Tyr Tyr Val Asn Lys Gln Glu Gly Lys Ser Leu
    450                 455                 460

Tyr Val Lys Gly Glu Pro Ile Ile Asn Phe Tyr Asp Pro Leu Ile Lys
465                 470                 475                 480

Arg Met Lys Gln Ile Glu Asp Lys Ile Glu Glu Ile Glu Ser Lys Gln
                485                 490                 495

Lys Lys Ile Glu Asn Glu Ile Ala Arg Ile Lys Lys Gly Asn Thr Asn
            500                 505                 510

Ser Gly Gly Ser Thr Thr Thr Ile Thr Asn Asn Asn Ser Gly Thr Asn
        515                 520                 525

Ser Ser Ser Thr Thr Tyr Thr Val Lys Ser Gly Asp Thr Leu Trp Gly
    530                 535                 540

Ile Ser Gln Arg Tyr Gly Ile Ser Val Ala Gln Ile Gln Ser Ala Asn
545                 550                 555                 560

Asn Leu Lys Ser Thr Ile Ile Tyr Ile Gly Gln Lys Leu Val Leu Thr
                565                 570                 575

Gly Ser Ala Ser Ser Thr Asn Ser Gly Gly Ser Asn Asn Ser Ala Ser
            580                 585                 590
```

```
Thr Thr Pro Thr Thr Ser Val Thr Pro Ala Lys Pro Thr Ser Gln Thr
        595                 600                 605

Thr Asp Tyr Lys Asp Asp Asp Asp Lys Ala Gly Pro Gly Trp Ser His
    610                 615                 620

Pro Gln Phe Glu Lys Gly Gly Gly Ser Gly Gly Gly Ser Gly Gly Gly
625                 630                 635                 640

Ser Trp Ser His Pro Gln Phe Glu Lys Gly Gly Gly Ser Gly Gly Gly
                645                 650                 655

Ser Gly Gly Gly Ser Trp Ser His Pro Gln Phe Glu Lys
            660                 665


<210> SEQ ID NO 7
<211> LENGTH: 65
<212> TYPE: DNA
<213> ORGANISM: Respiratory Syncytial Virus

<400> SEQUENCE: 7

atggggtctc tgcaaccgct ggccaccttg tacctgctgg ggatgctggt cgcttccgtg     60

ctagc                                                                 65


<210> SEQ ID NO 8
<211> LENGTH: 22
<212> TYPE: PRT
<213> ORGANISM: Respiratory Syncytial Virus

<400> SEQUENCE: 8

Met Gly Ser Leu Gln Pro Leu Ala Thr Leu Tyr Leu Leu Gly Met Leu
1               5                   10                  15

Val Ala Ser Val Leu Ala
            20


<210> SEQ ID NO 9
<211> LENGTH: 105
<212> TYPE: DNA
<213> ORGANISM: Respiratory Syncytial Virus

<400> SEQUENCE: 9

ctggtcttcc ctagcgacga gtttgatgcc tctatcagtc aggtgaacga aaaaatcaat     60

cagagcctgg cattcatccg aaagagcgac gaactgctgc acaac                    105


<210> SEQ ID NO 10
<211> LENGTH: 35
<212> TYPE: PRT
<213> ORGANISM: Respiratory Syncytial Virus

<400> SEQUENCE: 10

Leu Val Phe Pro Ser Asp Glu Phe Asp Ala Ser Ile Ser Gln Val Asn
1               5                   10                  15

Glu Lys Ile Asn Gln Ser Leu Ala Phe Ile Arg Lys Ser Asp Glu Leu
            20                  25                  30

Leu His Asn
        35


<210> SEQ ID NO 11
<211> LENGTH: 192
<212> TYPE: DNA
<213> ORGANISM: Respiratory Syncytial Virus

<400> SEQUENCE: 11

ttaattaatg actacaagga tgacgacgac aaggctggac ccggttggtc ccatccacag     60
```

```
ttcgagaagg gcggaggaag cggaggcggc tccggaggag gatcctggtc ccacccgcag    120

tttgagaagg gcggcggcag cggcggaggc tccggcggag gctcctggag ccacccccag    180

ttcgagaagt aa                                                        192


<210> SEQ ID NO 12
<211> LENGTH: 63
<212> TYPE: PRT
<213> ORGANISM: Respiratory Syncytial Virus

<400> SEQUENCE: 12

Leu Ile Asn Asp Tyr Lys Asp Asp Asp Asp Lys Ala Gly Pro Gly Trp
1               5                   10                  15

Ser His Pro Gln Phe Glu Lys Gly Gly Gly Ser Gly Gly Gly Ser Gly
            20                  25                  30

Gly Gly Ser Trp Ser His Pro Gln Phe Glu Lys Gly Gly Gly Ser Gly
        35                  40                  45

Gly Gly Ser Gly Gly Gly Ser Trp Ser His Pro Gln Phe Glu Lys
    50                  55                  60


<210> SEQ ID NO 13
<211> LENGTH: 314
<212> TYPE: DNA
<213> ORGANISM: Respiratory Syncytial Virus

<400> SEQUENCE: 13

gggaatacca actccggcgg gtctacaact accatcacaa acaataacag tggaactaac     60

agttcaagca caacttacac cgtgaagtct ggcgatacac tgtgggggat ctcacagcga    120

tatggcatca gcgtggctca gattcagtcc gcaaataacc tgaaatctac catcatctac    180

atcgggcaga agctggtgct gactggaagc gcctcctcta ccaacagtgg aggctcaaat    240

aactcagctt ccaccacacc aactaccagc gtgacccccg caaagcctac atcacagact    300

accgactaca agga                                                      314


<210> SEQ ID NO 14
<211> LENGTH: 101
<212> TYPE: PRT
<213> ORGANISM: Respiratory Syncytial Virus

<400> SEQUENCE: 14

Gly Asn Thr Asn Ser Gly Gly Ser Thr Thr Thr Ile Thr Asn Asn Asn
1               5                   10                  15

Ser Gly Thr Asn Ser Ser Ser Thr Thr Tyr Thr Val Lys Ser Gly Asp
            20                  25                  30

Thr Leu Trp Gly Ile Ser Gln Arg Tyr Gly Ile Ser Val Ala Gln Ile
        35                  40                  45

Gln Ser Ala Asn Asn Leu Lys Ser Thr Ile Ile Tyr Ile Gly Gln Lys
    50                  55                  60

Leu Val Leu Thr Gly Ser Ala Ser Ser Thr Asn Ser Gly Gly Ser Asn
65                  70                  75                  80

Asn Ser Ala Ser Thr Thr Pro Thr Thr Ser Val Thr Pro Ala Lys Pro
                85                  90                  95

Thr Ser Gln Thr Thr
            100


<210> SEQ ID NO 15
<211> LENGTH: 93
```

<212> TYPE: DNA
<213> ORGANISM: Respiratory Syncytial Virus

<400> SEQUENCE: 15 ttaattaaga ggatgaaaca gattgaggat aaaatcgagg aaattgaaag caagcagaag 60 aaaattgaga acgaaatcgc ccgcattaag aaa 93

<210> SEQ ID NO 16
<211> LENGTH: 31
<212> TYPE: PRT
<213> ORGANISM: Respiratory Syncytial Virus

<400> SEQUENCE: 16

Leu Ile Lys Arg Met Lys Gln Ile Glu Asp Lys Ile Glu Glu Ile Glu
1 5 10 15

Ser Lys Gln Lys Lys Ile Glu Asn Glu Ile Ala Arg Ile Lys Lys
20 25 30

<210> SEQ ID NO 17
<211> LENGTH: 1471
<212> TYPE: DNA
<213> ORGANISM: Respiratory Syncytial Virus

<400> SEQUENCE: 17 acagaatatc accgaggagt tttatcagag cacctgttca gccgtgagta agggctacct 60 gtcagcactg cggactggat ggtacaccag tgtgatcact attgagctgt caaacatcaa 120 ggaaaacaaa tgcaatggca ccgacgctaa ggtgaaactg attaagcagg agctggataa 180 gtacaaaaat gcagtgaccg aactgcagct gctgatgcag tcaacaccag cagctaacag 240 ccgagcacga agagagctgc cccgattcat gaactacaca ctgaacaaca ccaagaacac 300 aaatgtgact ctgagcaaga aacggaagag gcgcttcctg gggtttctgc tgggagtggg 360 atcagcaatc gccagcggca ttgccgtgag caaagtcctg cacctggagg gggaagtgaa 420 caagatcaaa tccgctctgc tgtctacaaa caaggcagtg gtcagtctgt caaatggcgt 480 gagtgtcctg acttcaaagg tgctggacct gaaaaattac atcgataagc agctgctgcc 540 tattgtcaac aaacagagct gttccatctc taatattgag accgtgatcg aattccagca 600 gaagaacaat agactgctgg agattacaag ggaattttct gtgaacgcag gcgtcaccac 660 acccgtgagt acatacatgc tgactaatag cgagctgctg tccctgatca acgacatgcc 720 tattaccaat gatcagaaga aactgatgtc caacaatgtg cagatcgtca gacagcagag 780 ttactcaatc atgtctatca ttaaggagga agtcctggct tacgtggtcc agctgccact 840 gtatggagtg atcgacacac cctgctggaa actgcatact tcacctctgt gcactaccaa 900 cacaaaggaa ggcagcaata tttgcctgac acgaactgac cggggatggt actgtgataa 960 cgccggcagc gtgtccttct ttccacaggc tgagacctgc aaggtccaga gcaacagggt 1020 gttctgtgac accatgaatt ctctgacact gcctagtgaa gtgaacctgt gcaatatcga 1080 catcttcaac ccaaagtacg attgtaagat catgacctct aagacagatg tcagctcctc 1140 tgtgatcact tccctggggg caatcgtgag ctgctacgga aagactaaat gtaccgcctc 1200 caacaaaaat cgcgggatca ttaagacctt cagcaacgga tgcgactatg tctccaacaa 1260 gggcgtggat actgtgagtg tcgggaacac cctgtactat gtcaataagc aggagggaaa 1320 aagcctgtac gtgaagggcg aacccatcat taacttttat gatcccctgg tcttccctag 1380 cgacgagttt gatgcctcta tcagtcaggt gaacgaaaaa atcaatcaga gcctggcatt 1440

```
catccgaaag agcgacgaac tgctgcacaa c                                  1471


<210> SEQ ID NO 18
<211> LENGTH: 490
<212> TYPE: PRT
<213> ORGANISM: Respiratory Syncytial Viru

<400> SEQUENCE: 18

Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
    50                  55                  60

Val Thr Glu Leu Gln Leu Leu Met Gln Ser Thr Pro Ala Ala Asn Ser
65                  70                  75                  80

Arg Ala Arg Arg Glu Leu Pro Arg Phe Met Asn Tyr Thr Leu Asn Asn
                85                  90                  95

Thr Lys Asn Thr Asn Val Thr Leu Ser Lys Lys Arg Lys Arg Arg Phe
            100                 105                 110

Leu Gly Phe Leu Leu Gly Val Gly Ser Ala Ile Ala Ser Gly Ile Ala
        115                 120                 125

Val Ser Lys Val Leu His Leu Glu Gly Glu Val Asn Lys Ile Lys Ser
    130                 135                 140

Ala Leu Leu Ser Thr Asn Lys Ala Val Val Ser Leu Ser Asn Gly Val
145                 150                 155                 160

Ser Val Leu Thr Ser Lys Val Leu Asp Leu Lys Asn Tyr Ile Asp Lys
                165                 170                 175

Gln Leu Leu Pro Ile Val Asn Lys Gln Ser Cys Ser Ile Ser Asn Ile
            180                 185                 190

Glu Thr Val Ile Glu Phe Gln Gln Lys Asn Asn Arg Leu Leu Glu Ile
        195                 200                 205

Thr Arg Glu Phe Ser Val Asn Ala Gly Val Thr Thr Pro Val Ser Thr
    210                 215                 220

Tyr Met Leu Thr Asn Ser Glu Leu Leu Ser Leu Ile Asn Asp Met Pro
225                 230                 235                 240

Ile Thr Asn Asp Gln Lys Lys Leu Met Ser Asn Asn Val Gln Ile Val
                245                 250                 255

Arg Gln Gln Ser Tyr Ser Ile Met Ser Ile Ile Lys Glu Glu Val Leu
            260                 265                 270

Ala Tyr Val Val Gln Leu Pro Leu Tyr Gly Val Ile Asp Thr Pro Cys
        275                 280                 285

Trp Lys Leu His Thr Ser Pro Leu Cys Thr Thr Asn Thr Lys Glu Gly
    290                 295                 300

Ser Asn Ile Cys Leu Thr Arg Thr Asp Arg Gly Trp Tyr Cys Asp Asn
305                 310                 315                 320

Ala Gly Ser Val Ser Phe Phe Pro Gln Ala Glu Thr Cys Lys Val Gln
                325                 330                 335

Ser Asn Arg Val Phe Cys Asp Thr Met Asn Ser Leu Thr Leu Pro Ser
            340                 345                 350

Glu Val Asn Leu Cys Asn Ile Asp Ile Phe Asn Pro Lys Tyr Asp Cys
        355                 360                 365
```

```
Lys Ile Met Thr Ser Lys Thr Asp Val Ser Ser Ser Val Ile Thr Ser
    370                 375                 380

Leu Gly Ala Ile Val Ser Cys Tyr Gly Lys Thr Lys Cys Thr Ala Ser
385                 390                 395                 400

Asn Lys Asn Arg Gly Ile Ile Lys Thr Phe Ser Asn Gly Cys Asp Tyr
                405                 410                 415

Val Ser Asn Lys Gly Val Asp Thr Val Ser Val Gly Asn Thr Leu Tyr
            420                 425                 430

Tyr Val Asn Lys Gln Glu Gly Lys Ser Leu Tyr Val Lys Gly Glu Pro
        435                 440                 445

Ile Ile Asn Phe Tyr Asp Pro Leu Val Phe Pro Ser Asp Glu Phe Asp
    450                 455                 460

Ala Ser Ile Ser Gln Val Asn Glu Lys Ile Asn Gln Ser Leu Ala Phe
465                 470                 475                 480

Ile Arg Lys Ser Asp Glu Leu Leu His Asn
                485                 490


<210> SEQ ID NO 19
<211> LENGTH: 1365
<212> TYPE: DNA
<213> ORGANISM: Respiratory Syncytial Virus

<400> SEQUENCE: 19

cagaatatca ccgaggagtt ttatcagtcc acctgttccg cagtgtccaa aggctatctg     60

tccgccctga gaaccggctg gtatacaagt gtgatcacta ttgagctgtc aaacatcaag    120

gaaaacaaat gcaatggcac cgacgctaag gtgaaactga ttaagcagga gctggataag    180

tacaaaaatg cagtgaccga actgcagctg ctgatgcagt caacaccagc cgctaacagc    240

aaagccaaga aagagctgcc ccggttcatg aattatacac tgaacaatac caagaacaca    300

aatgtgactc tgagcaagaa aaagaaaaag aaattcctgg ggtttctgct gggagtggga    360

tcagcaatcg ccagcggcat tgccgtgagc aaagtcctgc acctggaggg ggaagtgaac    420

aagatcaaat ccgctctgct gtctacaaac aaggcagtgg tcagtctgtc aaatggcgtg    480

agtgtcctga cttcaaaggt gctggacctg aaaaattaca tcgataagca gctgctgcct    540

attgtcaaca aacagagctg ttccatctct aatattgaga ccgtgatcga attccagcag    600

aagaacaata ggctgctgga gattacacgc gaattttctg tgaacgcagg cgtcaccaca    660

cccgtgagta catacatgct gactaatagc gagctgctgt ccctgatcaa cgacatgcct    720

attaccaatg atcagaagaa actgatgtcc aacaatgtgc agatcgtccg gcagcagagt    780

tactcaatca tgtctatcat taaggaggaa gtcctggctt acgtggtcca gctgccactg    840

tatggagtga tcgacacacc ctgctggaaa ctgcatacta gccccctgtg cactaccaac    900

acaaaggaag gcagcaatat ttgcctgaca cggactgaca gaggatggta ctgtgataac    960

gccggcagcg tgtccttctt tccacaggct gagacctgca aggtccagag caaccgagtg   1020

ttctgtgaca ccatgaattc tctgacactg cctagtgaag tgaacctgtg caatatcgac   1080

atcttcaacc caaagtacga ttgtaagatc atgacctcta agacagatgt cagctcctct   1140

gtgatcactt ccctgggggc aatcgtgagc tgctacggaa agactaaatg taccgcctcc   1200

aacaaaaata gagggatcat taagaccttc agcaacggat gcgactatgt ctccaacaag   1260

ggcgtggata ctgtgagtgt cgggaacacc ctgtactatg tcaataagca ggagggaaaa   1320

agcctgtacg tgaagggcga acccatcatt aacttttatg atccc                   1365
```

<210> SEQ ID NO 20
<211> LENGTH: 455
<212> TYPE: PRT
<213> ORGANISM: Respiratory Syncytial Virus

<400> SEQUENCE: 20

Gln Asn Ile Thr Glu Glu Phe Tyr Gln Ser Thr Cys Ser Ala Val Ser
1 5 10 15

Lys Gly Tyr Leu Ser Ala Leu Arg Thr Gly Trp Tyr Thr Ser Val Ile
20 25 30

Thr Ile Glu Leu Ser Asn Ile Lys Glu Asn Lys Cys Asn Gly Thr Asp
35 40 45

Ala Lys Val Lys Leu Ile Lys Gln Glu Leu Asp Lys Tyr Lys Asn Ala
50 55 60

Val Thr Glu Leu Gln Leu Leu Met Gln Ser Thr Pro Ala Ala Asn Ser
65 70 75 80

Lys Ala Lys Lys Glu Leu Pro Arg Phe Met Asn Tyr Thr Leu Asn Asn
85 90 95

Thr Lys Asn Thr Asn Val Thr Leu Ser Lys Lys Lys Lys Lys Lys Phe
100 105 110

Leu Gly Phe Leu Leu Gly Val Gly Ser Ala Ile Ala Ser Gly Ile Ala
115 120 125

Val Ser Lys Val Leu His Leu Glu Gly Glu Val Asn Lys Ile Lys Ser
130 135 140

Ala Leu Leu Ser Thr Asn Lys Ala Val Val Ser Leu Ser Asn Gly Val
145 150 155 160

Ser Val Leu Thr Ser Lys Val Leu Asp Leu Lys Asn Tyr Ile Asp Lys
165 170 175

Gln Leu Leu Pro Ile Val Asn Lys Gln Ser Cys Ser Ile Ser Asn Ile
180 185 190

Glu Thr Val Ile Glu Phe Gln Gln Lys Asn Asn Arg Leu Leu Glu Ile
195 200 205

Thr Arg Glu Phe Ser Val Asn Ala Gly Val Thr Thr Pro Val Ser Thr
210 215 220

Tyr Met Leu Thr Asn Ser Glu Leu Leu Ser Leu Ile Asn Asp Met Pro
225 230 235 240

Ile Thr Asn Asp Gln Lys Lys Leu Met Ser Asn Asn Val Gln Ile Val
245 250 255

Arg Gln Gln Ser Tyr Ser Ile Met Ser Ile Ile Lys Glu Glu Val Leu
260 265 270

Ala Tyr Val Val Gln Leu Pro Leu Tyr Gly Val Ile Asp Thr Pro Cys
275 280 285

Trp Lys Leu His Thr Ser Pro Leu Cys Thr Thr Asn Thr Lys Glu Gly
290 295 300

Ser Asn Ile Cys Leu Thr Arg Thr Asp Arg Gly Trp Tyr Cys Asp Asn
305 310 315 320

Ala Gly Ser Val Ser Phe Phe Pro Gln Ala Glu Thr Cys Lys Val Gln
325 330 335

Ser Asn Arg Val Phe Cys Asp Thr Met Asn Ser Leu Thr Leu Pro Ser
340 345 350

Glu Val Asn Leu Cys Asn Ile Asp Ile Phe Asn Pro Lys Tyr Asp Cys
355 360 365

Lys Ile Met Thr Ser Lys Thr Asp Val Ser Ser Ser Val Ile Thr Ser
370 375 380

-continued

```
Leu Gly Ala Ile Val Ser Cys Tyr Gly Lys Thr Lys Cys Thr Ala Ser
385                 390                 395                 400

Asn Lys Asn Arg Gly Ile Ile Lys Thr Phe Ser Asn Gly Cys Asp Tyr
                405                 410                 415

Val Ser Asn Lys Gly Val Asp Thr Val Ser Val Gly Asn Thr Leu Tyr
            420                 425                 430

Tyr Val Asn Lys Gln Glu Gly Lys Ser Leu Tyr Val Lys Gly Glu Pro
        435                 440                 445

Ile Ile Asn Phe Tyr Asp Pro
    450                 455
```

The invention claimed is:

1. A heat-stable oligomeric recombinant polypeptide presenting at least one antigenic epitope of the pre-fusion Respiratory Syncytial Virus F protein, said polypeptide comprising the Respiratory Syncytial Virus F protein ectodomain, from which the HRB region is deleted, and

[from which the transmembrane and cytoplasmic domains are deleted and replaced with] *which Respiratory Syncytial Virus F protein ectodomain is extended with* a heterologous trimerization domain[.] *that replaces the deleted Respiratory Syncytial Virus F protein transmembrane and cytoplasmic domains;* and wherein the two multibasic furin cleavage sites in said Respiratory Syncytial Virus F protein ectodomain are mutated by the substitution of all [lysine] *arginine* residues in said sites with [arginine] *lysine* residues, thereby rendering said furin cleavage sites defective.

2. The heat-stable oligomeric recombinant polypeptide according to claim 1, wherein said heterologous trimerization domain is a GCN4 leucine zipper trimerization motif.

3. The heat-stable oligomeric recombinant polypeptide according to claim 1, wherein said deletion of the HRB region comprises a deletion of the HRB wherein the [HBR] *HRB* comprises the sequence of SEQ ID NO: 10.

4. The heat-stable oligomeric recombinant polypeptide according to claim 1, further comprising a LysM peptidoglycan binding domain linked to the carboxy-terminal end of said trimerization domain.

5. The heat-stable oligomeric recombinant polypeptide according to claim 1, further comprising a triple Strep-tag.

6. The heat-stable oligomeric recombinant polypeptide according to claim 1, wherein said ectodomain is a soluble ectodomain.

7. The heat-stable oligomeric recombinant polypeptide according to claim 1, wherein said antigenic epitope is recognized by a pre-fusion specific monoclonal antibody AM22 or D25, or AM22 and D25.

8. An immunogenic composition comprising the oligomeric recombinant polypeptide of claim 1.

9. An immunogenic composition according to claim 8, further comprising an adjuvant.

10. An immunogenic composition according to claim 8, in wherein said oligomeric recombinant polypeptide is bound, covalently or non-covalently, to a carrier particle.

11. An immunogenic composition according to claim 10, wherein said carrier particle is a bacterium-like particle.

12. A recombinant expression vector comprising a nucleotide sequence encoding the polypeptide forming the heat-stable oligomer of claim 1.

13. A method of inducing an immune response in a subject to RSV comprising administering to said subject an immunogenic composition according to claim 8.

*14. A heat-stable oligomeric recombinant polypeptide presenting at least one antigenic epitope of the pre-fusion Respiratory Syncytial Virus F protein, said polypeptide comprising*

*the Respiratory Syncytial Virus F protein ectodomain, which is extended with a heterologous trimerization domain that replaces the deleted Respiratory Syncytial Virus F protein transmembrane and cytoplasmic domains; and*

*wherein the two multibasic furin cleavage sites in said Respiratory Syncytial Virus F protein ectodomain are mutated by the substitution of all arginine residues in said sites with lysine residues, thereby rendering said furin cleavage sites defective.*

*15. The heat-stable oligomeric recombinant polypeptide according to claim 14, wherein said heterologous trimerization domain is a GCN4 leucine zipper trimerization motif.*

*16. The heat-stable oligomeric recombinant polypeptide according to claim 14, further comprising a LysM peptidoglycan binding domain linked to the carboxy-terminal end of said trimerization domain.*

*17. The heat-stable oligomeric recombinant polypeptide according to claim 14, further comprising a triple Strep-tag.*

*18. The heat-stable oligomeric recombinant polypeptide according to claim 14, wherein said ectodomain is a soluble ectodomain.*

*19. The heat-stable oligomeric recombinant polypeptide according to claim 14, wherein said antigenic epitope is recognized by a pre-fusion specific monoclonal antibody AM22 or D25, or AM22 and D25.*

*20. An immunogenic composition comprising the oligomeric recombinant polypeptide of claim 14.*

*21. An immunogenic composition according to claim 20, further comprising an adjuvant.*

*22. An immunogenic composition according to claim 20, in wherein said oligomeric recombinant polypeptide is bound, covalently or non-covalently, to a carrier particle.*

*23. An immunogenic composition according to claim 22, wherein said carrier particle is a bacterium-like particle.*

*24. A recombinant expression vector comprising a nucleotide sequence encoding the polypeptide forming the heat-stable oligomer of claim 14.*

*25. A method of inducing an immune response in a subject to RSV comprising administering to said subject an immunogenic composition according to claim 20.*

* * * * *